(12) United States Patent
Hishikawa

(10) Patent No.: US 6,808,161 B1
(45) Date of Patent: Oct. 26, 2004

(54) CONNECTOR

(75) Inventor: Yoshinori Hishikawa, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 162 days.

(21) Appl. No.: 10/088,416

(22) PCT Filed: Sep. 18, 2000

(86) PCT No.: PCT/JP00/06358

§ 371 (c)(1),
(2), (4) Date: Jul. 9, 2002

(87) PCT Pub. No.: WO01/20218

PCT Pub. Date: Mar. 22, 2001

(30) Foreign Application Priority Data

Sep. 16, 1999 (JP) .......................................... 11-262079

(51) Int. Cl.[7] .............................. F16L 29/02; A61M 5/14
(52) U.S. Cl. ............................... 251/149.1; 604/167.04
(58) Field of Search .......................... 251/149.1, 149.3; 604/167.04

(56) References Cited

U.S. PATENT DOCUMENTS

| 5,295,657 A | * | 3/1994 | Atkinson ................. 251/149.1 |
| 5,295,658 A | * | 3/1994 | Atkinson et al. ........ 251/149.1 |
| 5,501,426 A | * | 3/1996 | Atkinson et al. ........ 251/149.1 |
| 5,533,708 A | * | 7/1996 | Atkinson et al. ........ 251/149.1 |
| 5,676,346 A | | 10/1997 | Leinsing |
| 6,050,978 A | * | 4/2000 | Orr et al. ................... 604/249 |

FOREIGN PATENT DOCUMENTS

| JP | 7-502420 A | 3/1995 |
| JP | 7-502421 A | 3/1995 |
| JP | 8-500983 A | 2/1996 |
| JP | 8-243092 A | 9/1996 |
| JP | 9-108361 A | 4/1997 |
| JP | 10-118178 A | 5/1998 |
| JP | 10-512946 A | 12/1998 |
| WO | 89/06553 A2 | 7/1989 |
| WO | 90/11103 A2 | 10/1990 |
| WO | 93/05838 A1 | 4/1993 |
| WO | 93/05839 A1 | 4/1993 |
| WO | 93/24174 A1 | 12/1993 |
| WO | 95/03509 A2 | 2/1995 |
| WO | 96/23158 A1 | 8/1996 |

* cited by examiner

Primary Examiner—Paul J. Hirsch
(74) Attorney, Agent, or Firm—Burns, Doane, Swecker & Mathis, L.L.P.

(57) ABSTRACT

A connector used for various medical instruments, infusion containers, and infusion devices to connect a tube. The connector includes a cylindrical valve made of elastic material with a closable slit so that a tube can be connected without passing through the valve.

17 Claims, 13 Drawing Sheets

FIG.1
FIG.2
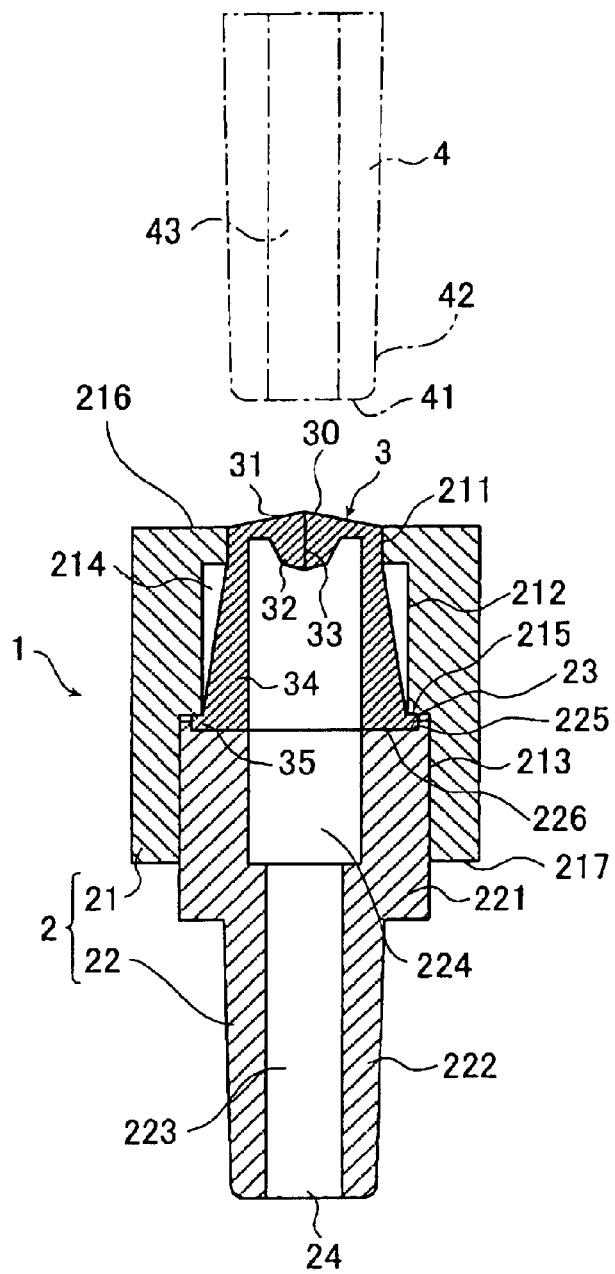
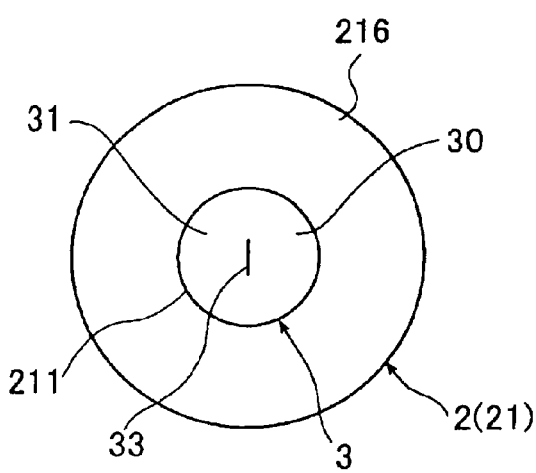

FIG.7A
FIG.7B
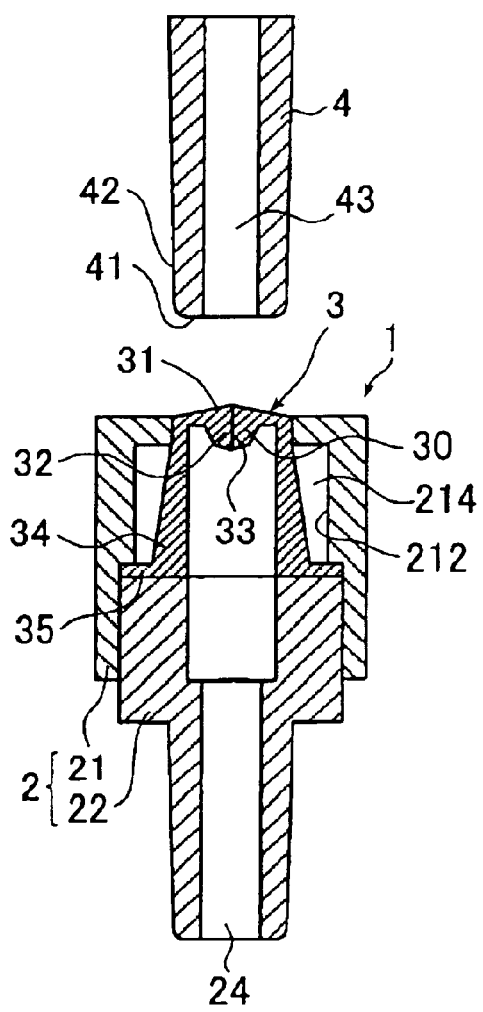
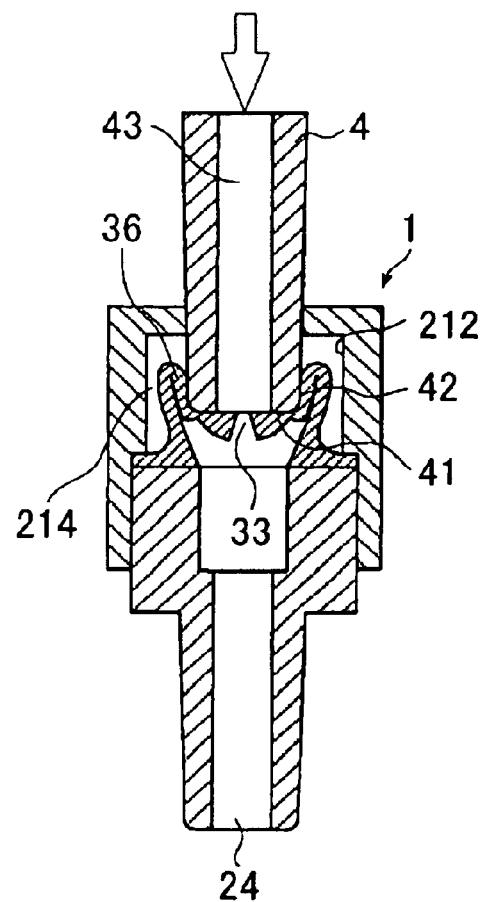

FIG.9
FIG.10
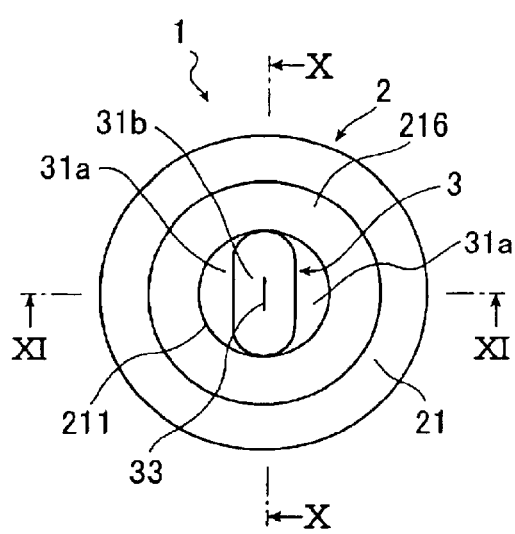
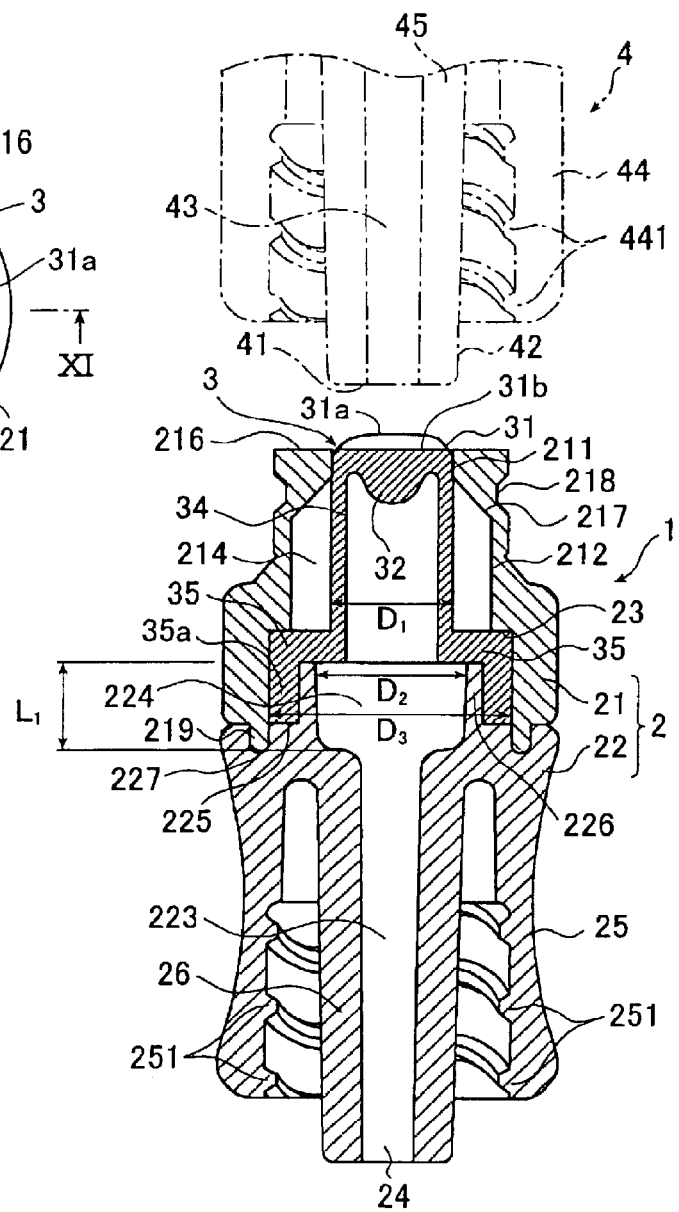

CONNECTOR

TECHNICAL FIELD

This invention relates to a connector for connecting tubular bodies, which is adapted for use with various medical devices, infusion containers, fluid feeding device, and the like.

BACKGROUND ART

This invention relates to a connector (an adapter) which is used for connecting tubular bodies, and which is adapted for use with various medical devices, infusion containers, fluid feeding device, and the like.

The connector of this type has been fabricated so that the connector comprises a housing formed with a fluid passage, and a valve of an elastic material which is mounted on the tube connection port of the housing. Such connector has been used to reliably communicate the fluid passages defined in the tube and in the connector once the valve has been opened by the valve-opening/closing mechanism so that the fluid (liquid and the like) flowing through the tube can be sent into the connector.

Among such connectors, the connectors used for medical applications suffer from the risk of bloodborne infection due to unintentional accidents, and it is highly desirable in such a connector to avoid the opening of the valve with a sharp needle. Use of a reclosable, "needleless" connector is seriously in demand.

Such connector of the first type has a valve provided with a slit or the like which remains closed when no tube or the like is engaged. This valve is opened by penetrating a tubular body such as a cannula, a male Luer, or the like through the valve to thereby communicate the fluid passages defined in the tubular body and in the connector. Typical examples of such connector are disclosed in JP 08-243092 A, JP 08-500983 A, JP 10-512946 A, and JP 10-118178 A.

Second type of such connector is disclosed, for example, in JP 09-108361 A. The connector of JP 09-108361 A comprises a valve comprising an elliptical piston head formed with an opening (marquise-shaped bore) therethrough, and a housing provided with a connection port having a diameter smaller than said head. When no tube is connected, the elliptical head is constrained in the reduced diameter housing by the piston to shut the bore. Once the tube is connected, the piston retreats into the enlarged diameter housing by being pushed with the distal surface of the tube, and the head regains its natural elliptic shape and the marquise-shaped bore similarly regains its open shape to provide a fluid passage therethrough. Another example of the connector wherein the tube does not penetrate through the valve is a connector of the constitution including a drive means such as tapered female threads for compressing the valve. JP 07-502420 A discloses a connector wherein the valve is compressed and deformed to open the valve slit by means of the tapered female threads. JP 07-502421 A discloses a connector comprising a valve having a bias means of pleated shape and a cap, and an urging portion (a female fastener) for opening/closing the valve, wherein the fluid passage is closed by the blocking of the artificial opening defined in the valve-retaining member by the valve cap and the adjacent shoulder of the biasing portion which are pushed by the urging means. On the other hand, when the cap is compressed from the exterior by a syringe to open the artificial opening, a fluid passage is defined by the notch (guide slots) extending in the direction of the fluid passage formed on the biasing portion and the bypass openings.

However, the connectors of the first type wherein the valve is forced open by the tube penetration through the valve suffers from the problem of excessive increase of the diameter of the opening. In the case of the connector having an opening that has been preliminarily formed, the connector suffers from the problem of fluid leakage due to the reverse flow of the fluid from the proximal end of the connector upon disengagement of the tube from the connector.

Furthermore, the connectors of the type wherein the distal end of the tube enters the interior of the connector by the penetration of the tube through the valve suffer from the problem of contamination of the fluid passage of the connector by the bacteria which had been attached on the distal end of the tube.

The connectors of the second type do not suffer from the problems of the first type connectors since the tube does not penetrate through the valve. These connectors, however, needs further improvements in their sealing capability and engagement reliability. To be more specific, the connectors of the second type has a structure wherein the distal end surface of the tube is pushed against the proximal surface of the valve, and the liquid tightness is predominantly dependent on the contact pressure between the distal end surface of the tube and the proximal surface of the valve. As a consequence, such connector is associated with the risk of fluid leakage upon increase in the inner pressure. There is also a risk of disengagement between the tube and the valve unless they are pushed against each other with a very strong force.

DISCLOSURE OF THE INVENTION

In view of the situation as described above, an object of the present invention is to provide a connector which has a simple structure comprising a small number of components, which is easy to use, which is free from fluid passage contamination upon engagement with the tube, which has enabled a reliable engagement between the tube and the connector with high liquid tightness (with high sealing capability), and which has avoided fluid leakage from the connector during the engagement and after the disengagement of the tube with the connector.

Such an object of the present invention is achieved by the present invention as described below in the following (1) to (17). It is also preferable that the present invention is as described in the following (18) and (19).

(1) A connector comprising
a housing provided with a fluid passage in its interior and a connection port for engagement with a tube; and
a valve of an elastic material accommodated in said housing; wherein
said valve has a cylindrical base; a valve portion on one axial end of said base which becomes in contact with said tube to be pushed inward by said tube; and a slit formed in said valve portion which opens when said valve portion is pushed inward; and
said valve undergoes elastic deformation when said tube is engaged with said connection port of the housing by pushing said tube against said valve portion of the valve, and said slit opens as a result of said elastic deformation such that said valve portion becomes in close contact with distal end surface and distal peripheral surface of said tube.

(2) A connector comprising
a housing provided with a fluid passage in its interior and a connection port for engagement with a tube; and
a valve of an elastic material accommodated in said housing; wherein said valve has a cylindrical base; a valve portion on one axial end of said base which becomes in contact with said tube to be pushed inward by said tube; and a slit formed in said valve portion which opens when said valve portion is pushed inward; and said valve undergoes elastic deformation when said tube is engaged with said connection port of the housing by pushing said tube against said valve portion of the valve, and said slit opens as a result of said elastic deformation and said base becomes folded such that said valve portion enters the interior of said vase and a new interior surface defined by the folded valve portion becomes in close contact with distal peripheral surface of said tube.

(3) A connector comprising a housing provided with a fluid passage in its interior and a connection port for engagement with a tube; and a valve of an elastic material accommodated in said housing; wherein said valve has a cylindrical base; a valve portion on one axial end of said base which becomes in contact with said tube to be pushed inward by said tube; and a slit formed in said valve portion which opens when said valve portion is pushed inward; and said valve undergoes elastic deformation when said tube is engaged with said connection port of the housing by pushing said tube against said valve portion of the valve, and said slit opens as a result of said elastic deformation such that said base becomes compressed in the axial direction to become dilated.

(4) A connector comprising a housing provided with a fluid passage in its interior and a connection port for engagement with a tube; and a valve of an elastic material accommodated in said housing; wherein said valve has a cylindrical base; a valve portion on one axial end of said base which becomes in contact with said tube to be pushed inward by said tube; and a slit formed in said valve portion which opens when said valve portion is pushed inward; and said valve undergoes elastic deformation when said tube is engaged with said connection port of the housing by pushing said tube against said valve portion of the valve, and said slit opens as a result of said elastic deformation such that said valve portion becomes in close contact with said tube and the area of contact enters the interior of said base.

(5) A connector comprising a housing provided with a fluid passage in its interior and a connection port for engagement with a tube; and a valve of an elastic material accommodated in said housing; wherein said valve has a cylindrical base; a valve portion on one axial end of said base which becomes in contact with said tube to be pushed inward by said tube; and a slit formed in said valve portion which opens when said valve portion is pushed inward; and said valve undergoes elastic deformation when said tube is engaged with said connection port of the housing by pushing said tube against said valve portion of the valve, and said slit opens as a result of said elastic deformation with the base being dilated; and a space is defined between said base and said housing to allow said dilatation of the base.

(6) A connector comprising a housing provided with a fluid passage in its interior and a connection port for engagement with a tube; and a valve of an elastic material accommodated in said housing; wherein said valve has a cylindrical base; a valve portion on one axial end of said base which becomes in contact with said tube to be pushed inward by said tube; a slit formed in said valve portion which opens when said valve portion is pushed inward; and a fixture portion on the other axial end of said base, said fixture portion securing said valve against said housing; and said housing has a relief space defined in its interior to thereby allow moving of fixture side of said base into said relief space;

said valve undergoes elastic deformation when said tube is engaged with said connection port of the housing by pushing said tube against said valve portion of the valve, and said slit opens as a result of said elastic deformation with the fixture side of said base being pushed into said relief space.

(7) A connector according to the above (6) wherein said base becomes compressed in the axial direction to become dilated when said tube is pushed against said valve portion of the valve.

(8) A connector according to the above (6) or (7) wherein a space is defined between said base and said housing to allow said dilatation of said base.

(9) A connector according to any one of the above (1) to (6) wherein said valve restores its original shape when said tube is disengaged from said connection port.

(10) A connector according to any one of the above (1) to (6) wherein said slit has a size such that penetration of said tube through said slit upon opening of said slit is not allowed.

(11) A connector according to the above (10) wherein said valve portion has a thick area in the central region, and said slit is formed in said thick area.

(12) A connector according to any one of the above (1) to (6) wherein at least a part of said base is tapered such that outer diameter or inner diameter increases with increase in the distance from said valve portion.

(13) A connector according to any one of the above (1) to (6) wherein said valve portion has a projection and/or a recess on the surface that becomes in contact with distal end surface of said tube.

(14) A connector according to the above (13) wherein said valve portion has a first projection on the surface that becomes in contact with said distal end surface of the tube.

(15) A connector according to the above (14) wherein said first projection has a shape resembling a dome.

(16) A connector according to any one of the above (1) to (15) wherein said valve portion has a projection on the surface that does not become in contact with said distal end surface of the tube.

(17) A connector according to the above (16) wherein said projection constitutes a part of a sphere.

(18) A connector according to any one of the above (1) to (17) wherein said housing is formed in its interior with a space, and said valve is formed on its exterior periphery with a flange, and said flange of the valve is engaged in said space of the housing.

(19) A connector according to the above (18) wherein said housing comprises two members, and said flange is inserted in the space formed between said two members so that said valve is fixedly secured to said housing.

BRIEF DESCRIPTION OF THE DRAWINGS

FIG. 1 is a longitudinal cross section of the connector according to an embodiment of the present invention.

FIG. 2 is a plan view of the connector seen from proximal side.

FIG. 7 is a longitudinal cross section of a connector according to another embodiment of the present invention wherein the housing has a space defined in its interior to allow the dilatation of the valve.

FIG. 9 is a plan view of the connector according to another embodiment of the present invention seen from the proximal side.

FIG. 10 is a longitudinal cross section of the connector of FIG. 9 taken along the line X—X.

FIG. 15 is a longitudinal cross section of the embodiment of FIG. 11 showing the shape of the valve support and the like.

BEST MODE FOR CARRYING OUT THE INVENTION

Figure 3:
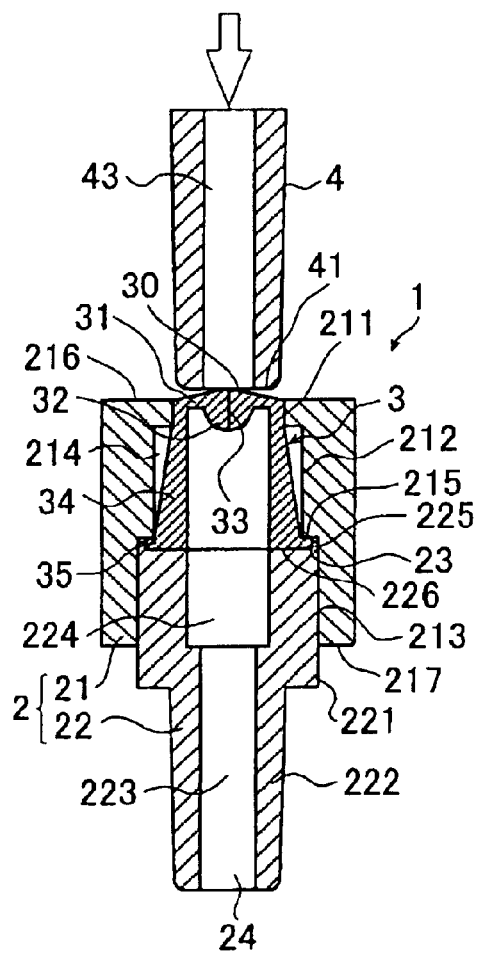
FIG. 3 is a longitudinal cross section of the connector of FIG. 1 and the tube when the distal end surface of the tube has been positioned on the connector.

Next, various embodiments of the present invention are described in detail by referring to the attached drawings. In the following description, the upper side of the connector (the side engaged to the tube) in longitudinal cross sections (for example, in FIG. 1, FIGS. 3 to 6, and other drawings corresponding to these drawings) is referred "proximal" whereas the lower side is referred as "proximal".

FIG. 1 is a longitudinal cross sectional view of the connector according to one embodiment of the present invention wherein an I-shaped connector used for connecting tubes is shown with some part of one tube. FIG. 2 is a plan view of the connector of FIG. 1 seen from the proximal side.

FIGS. 1 and 2 are views showing a connector 1 which is used for engagement of a tube 4. The connector 1 comprises a housing 2 and a valve 3.

The housing 2 comprises a cylinder 21 on its proximal side and a cylindrical cap 22 on its distal side, and the housing 1 is formed substantially in cylindrical shape with a passage for fluid (hereinafter referred as a fluid passage) 24 defined in its interior. The terms "cylinder" and "cap" are used herein for convenience of describing the two housing components, and there would be no problem if these components were designated in the reverse.

In the embodiment shown in FIG. 1, the cylinder 21 has a constant outer diameter from its proximal end 216 to its distal end 217. The cylinder 21, however, is defined in its interior with an intermediate diameter space 212 for accommodating base 34 of the valve 3 and a cap-securing area 213 of a larger diameter. The cylinder 21 also has a connection port 211 for engagement of the tube on its proximal end 216. The connection port 211 has a diameter which is smaller than the intermediate diameter space 212 so that the base of the valve 3 can snugly fit in its interior. When the valve 3 is accommodated in the intermediate diameter space 212, a space 214 remains in the intermediate diameter space 212, namely, between the housing and the base 34 to allow dilatation of the base 34.

The cap 22 has a proximal portion 221 with an outer diameter that enables securing of the cap 22 to the cap-securing area 213 of the cylinder 21. The cap 22 is formed with a valve-supporting area 226 on distal end 225 of the proximal portion 221. The cylinder 21 and the 22 may be engaged by any means as long as the cap-securing area 213 and the proximal portion 221 are reliably connected with each other. Typical means of the engagement include fitting (in particular, fitting with caulking and threading), bonding with an adhesive, and fusion such as heat fusion or ultrasonic fusion when both the cylinder 21 and the cap are made of resins.

Distal portion 222 of the cap 22 may have an outer diameter smaller than that of the proximal portion 221 in order to enable engagement with a flexible tube (not shown) or the like. The distal portion 222, however, may have a constant outer diameter, and alternatively, a Luer taper for facilitating smooth insertion into and liquid-tight engagement with the tube. One typical such tube (not shown) is the tube of an infusion set.

The distal portion 222 and the proximal portion 221 of the cap 22 are formed in their interior with a space 223 and a space 224, respectively, and these spaces 223 and 224 define a fluid passage 24 in the cap 22.

When the cylinder 21 and the cap 22 are connected, a groove 23 is defined all around the interior of the housing 2 as a space between shoulder 215 of the cylinder 21 and the distal end 225 of the cap 22.

The housing 2 as described above may comprise a resinous materials, and typical resinous materials include polyethylene, polypropyrene, ethylene-propylene copolymer, ethylene-vinyl acetate copolymer (EVA), and other polyolefins, polyvinyl chloride, polyvinylidene chloride, polystyrene, polyamide, polyimide, polyamideimide, polycarbonate, poly-(4-methylpentene-1), ionomer, acrylic resin, polymethylmethacrylate, acrylonitrile-butadiene-styrene copolymer (ABS resin), acrylonitrile-styrene copolymer (AS resin), butadiene-styrene copolymer, polyethylene terephthalate (PET), polybutylene terephthalate (PBT), polycyclohexane terephthalate (PCT), and other polyesters, polyether, polyether ketone (PEK), polyether etherketone (PEEK), polyether imide, polyacetal (POM), polyphenyleneoxide, modified polyphenyleneoxide, polysulfone, polyether sulfone, polyphenylene sulfide, polyallylate, aromatic polyester (liquid crystal polymer), polytetrafluoroethylene, polyvinylidene fluoride, and other fluororesins, a blend containig at least one of these, and a polymer alloy. The housing 2 may also comprise a glass material, ceramics, metal material, or a composite of such material with the resinous material as described above.

The cylinder 21 and the cap 22 may be formed either from the same material or from different materials.

The valve 3 in the connector of the present invention comprises the base 34 which is substantially cylindrical in shape and a valve portion 30 provided on the axially proximal side of the base 34, and the valve portion 30 is formed with a reclosable slit 33. When the slit 33 is closed (when no tubeis connected), this valve 3 blocks the fluid passage 24 of the housing 2 by shutting the inner cavity of the housing with the valve portion 30. When the tube 4 is engaged with the connector, the valve 3 is pushed by distal end surface 41 of the tube 4, and the slit 33 is opened to communicate fluid passage 43 of the valve 3 with the fluid passage 24 of the housing 2. When the slit 33 is open, distal end of the tube 4 is supported by the valve 3 itself which has undergone elastic deformation (which has been folded) by the pushing with the tube 4, and the tube 4 does not penetrate through the slit 33 (the valve portion 30). Therefore, the valve 3 can be opened without using a sharp needle, and the valve restores its original shape with the slit 33 being closed once the valve is liberated from the engagement with the tube 4.

The valve 3 having such unique reclosable mechanism is described in further detail.

The valve 3 is formed from an elastic material (flexible material) which may undergo an elastic deformation. Exemplary such elastic materials include rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluororubber as well as thermoplastic elastomers such as styrene rubber, polyolefin rubber, polyvinyl chloride rubber, polyurethane rubber, polyester rubber, polyamide rubber, polybutadiene rubber, transpolyisoprene rubber, fluororubber, and chlorinated polyethylene rubber.

The valve 3 may comprise a single material, or alternatively, a combination of two or more elastic materials each having different composition and properties (flexibility, flexural modulus, rubber hardness, etc.) that have been appropriately selected to realize the desired elasticity, abrasion properties, valve shape and size, and the like.

The valve 3 comprises the base 34 which has been formed in a hollow shape (and in particular, in a substantially cylindrical shape, hollow frustconical shape, or the like), and the valve portion 30 provided axially on one side (on the side of the proximal end 31) of the base 34 in order to shield the inner cavity of the base 34. The base 34 and the valve portion 30 are preferably formed as one integral member. The valve portion 30 may preferably have an outer diameter which is substantially the same or slightly larger than that of the distal end surface 41 of the tube 4 so that the valve portion 30 easily becomes folded inward with the slit 33 being opened when it is pushed by the distal end surface 41 of the tube 4.

In the present invention, the base 34 of the valve 3 is preferably tapered such that the wall thickness of the base 34 gradually increases toward the distal end of the base 34. The base 34 may be tapered either on the side of the inner cavity or on the outer surface, or on both sides, and either around the entire outer surface of the base 34 in on some part of the outer surface.

In the embodiment shown in FIG. 1, the base 34 is tapered on the outer surface. The inner diameter of the valve 3 is substantially constant from the proximal end to the distal end, and also substantially consistent with the diameter of the cap space 224 (inner diameter of the proximal portion 221) of the housing 2. The outer surface of the valve 3 is tapered with the diameter increasing from the side of the proximal surface 31 to the side of the distal flange 35 with the wall thickness of the base 34 gradually increasing toward the distal end. As a result of such configuration, the base 34 exhibits a lower flexural strength on the side of the proximal end compared to the side of the distal end, and a folded portion can be readily and reliably (with high reproducibility) formed when the valve portion 30 is pushed inward by the tube 4 as will be described below in further detail.

The proximal end of the base 34 has an outer diameter which is substantially the same as the diameter of the connection port 211 of the cylinder 21 so that the proximal end of the base 34 snugly fits in the connection port 211 of the cylinder 21.

The valve portion 30 of the valve 3 is the area which receives force of pushing by the distal end surface 41 of the tube. In the present invention, the central region of the valve portion 30 provided with the slit 33 is formed to have a greater thickness compared to the peripheral region of the valve portion 30 to thereby facilitate smooth opening of the slit 33 and bending of the base 34 into the intermediate diameter space 212, and also, reliable closure of the slit 33 in the connection port 211. In order to increase the thickness of the central region of the valve portion 30, a projection may be formed on at least one surface of the valve portion 31, either on the side of the proximal surface 31 that becomes in contact with the distal end surface 41 of the tube 4 or on the rear side. The projection is not limited for its shape. While the valve portion 30 may have either a projection and/or a recess on the side of the proximal surface 31, the valve portion 31 may preferably have a projection which protrudes beyond the proximal end 216 of the housing 2 at least at some part of the proximal surface 31.

In the embodiment shown in FIG. 1, first projection is formed on the proximal surface 31 of the valve portion 30. This first projection formed on the proximal surface 31 protrudes outward beyond the proximal end 216 of the housing 2, and resembles the shape of a dome (cone, lamp shade, or dish). The rear surface 32 of the valve portion 30 has second projection which protrudes in the direction opposite to that of the first projection formed on the proximal surface 31. This second projection has a shape that constitutes a part of a sphere.

In the central region (thick region) of the valve portion 30, there is formed the slit 33 which extends through the valve portion 30. The slit 33 is closed in its natural state (under the condition when no external force is applied thereto) due to the elasticity of the valve portion 30, and a liquid tight (and gas tight) condition is thereby maintained.

In the present invention, the slit 33 is formed to a size such that, even when the valve portion 30 is pushed in and the slit 33 has reached its largest size, opening of the slit is not any larger than the outer diameter of the tube 4 and penetration of the tube 4 therethrough is prohibited.

In the embodiment shown in the drawings, the slit 33 comprises a straight cut (slit) that has been made to extend between the ridge of the first projection on the proximal surface 31 and the ridge of the second projection on the side of the rear side 32 (see FIG. 2).

The slit 33 is closed by the elasticity of the valve portion 30 when no load is placed (under the absence of the external force) with the liquid tight state (gas tight state) maintained. In the present invention, the slit is formed in the thick region of the valve portion 30 to thereby realize excellent blockage (sealing) when the tube 4 is no longer engaged with the connector.

It is to be noted that the slit 33 does not necessarily extend in the direction shown in the drawings, and the shape of the slit 33 is also not limited to the straight slit.

The valve 3 is formed near the distal end of the base 34 with a flange 35 which has a larger outer diameter. The valve 3 which is supported by the valve-supporting area 226 of the housing 2 is secured to the housing 2 by the insertion or fitting of the flange 35 in the space (groove) 23 of the housing 2. In this embodiment, the valve 3 is secured to the housing 2 in a reliable (and in particular, in a liquid tight) manner by the sandwiching of the flange 35 between the shoulder 215 of the cylinder 21 and the valve-supporting area 226 of the cap 22.

The proximal surface 31 of the valve 3 secured to the housing as described above extends beyond the proximal end 216 of the housing 2, and such constitution is preferable since convenient disinfection is enabled.

Next, mechanism of engagement between the connector 1 of the present invention and the tube 4 is described in detail by referring to the drawings.

As described above, the connector 1 opens and closes the fluid passage 24 of the housing 2 by the opening and closing of the slit 33.

FIGS. 3 to 6 are longitudinal cross sectional views corresponding to FIG. 1, and they describe the action mechanism when the tube 4 is engaged with the connector 1 by showing various phases in sequence. In FIGS. 3 to 6, the numerals which are in common with FIGS. 1 and 2 designate the same member.

The tube 4 of this embodiment is a part of a device or the device itself which is to be connected to the connection port (small diameter area) 221 of the connector 1. Examples of such tube 4 are distal tip (the site to which needle is attached) of a syringe, and independent tubular device such as a hub or a sheath. Such tube 4 may typically comprise a material similar to those used for the cylinder 21 and the cap 22 as described above.

The tube 4 may preferably have a fluid passage in its interior and a Luer tapered outer surface. In other words, the distal end of the tube 4 may have an outer diameter which is slightly smaller than the diameter of the opening (the connection port diameter) of the connection port 211 of the cylinder 21, and the outer surface of the tube 4 may be tapered with the outer diameter gradually increasing toward the proximal end such that the proximal end of the tube 4 has an outer diameter which is larger than the diameter of the connection port 211. As a result of such constitution, the distal end of the tube 4 can be inserted in the housing 2 from the connection port 211 and through the valve 3, and also, the distal end of the tube 4 can be fitted in the connection port 211 to any desired depth.

FIG. 3 is a longitudinal cross sectional view when the distal end surface 41 of the tube 4 has been positioned on the connector 1. As described above, the slit 33 of the valve 3 is closed when there is no load on (when no external force is applied to) the valve 3, and the liquid tight condition is thereby maintained.

In the housing 2 wherein the base 34 of the valve 3 is inserted through the connection port 211, there is formed the space 214. As will be described below, the space 214 functions as a space which allows dilatation of the base 34 when it is compressed in axial direction during the engagement of the tube 4, and it also functions as a space to allow the formation of the folded portion 36.

Next, the tube 4 is positioned as shown in FIG. 3 so that the central axis of the tube 4 is in alignment with the central axis of the housing 2, and the tube 4 is moved in distal direction (in the direction shown by the arrow in the drawings) for insertion into the connector 1.

Figure 4:
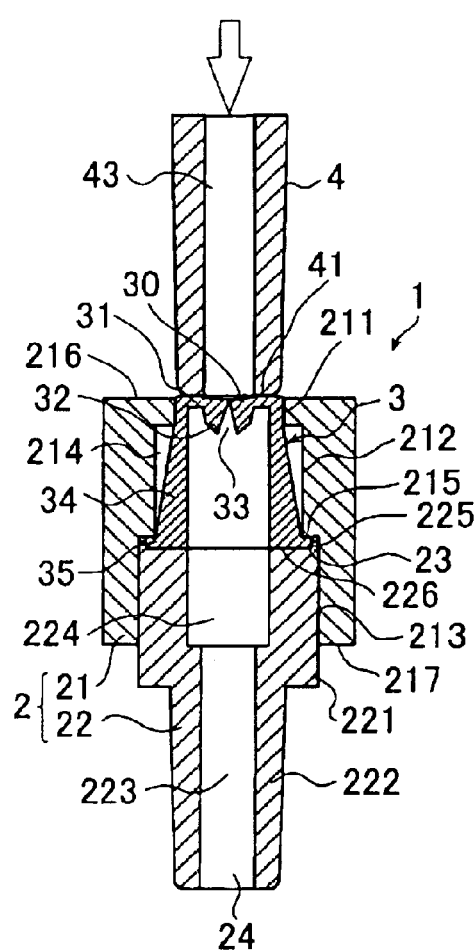
FIG. 4 is a longitudinal cross section of the connector of FIG. 1 and the tube when the distal end surface of the tube has proceeded to the level of the proximal end surface of the housing.

FIG. 4 shows the state when the distal end surface 41 of the tube 4 has substantially reached the level of the proximal end 216 of the housing 2 (the cylinder 21). When the tube 4 is at this position, it is mainly the valve portion 30 that has started the deformation by the pushing with the tube 4.

Referring to FIG. 4, when the first projection on the valve portion 30 (the proximal surface 31) of the valve 3 is pushed by the distal end surface 41 of the tube 4, the proximal surface 31 of the valve 3 mainly undergoes an elastic deformation since dilatation of the proximal surface 31 is restricted by the cylinder 21 of the connection port 211. To be more specific, the first projection on the proximal surface 31 gradually changes its shape from the dome shape to a flat surface, and the flat surface is then recurved to become recessed.

With the deformation of the proximal surface 31, the slit 33 that had been shut starts opening from the side of the second projection on the rear surface 32. The first projection of dome shape is turned into a flat surface, and then, recurved into a recess only by pushing the tube 4 against the proximal surface 31 with a slight force.

Figure 5:
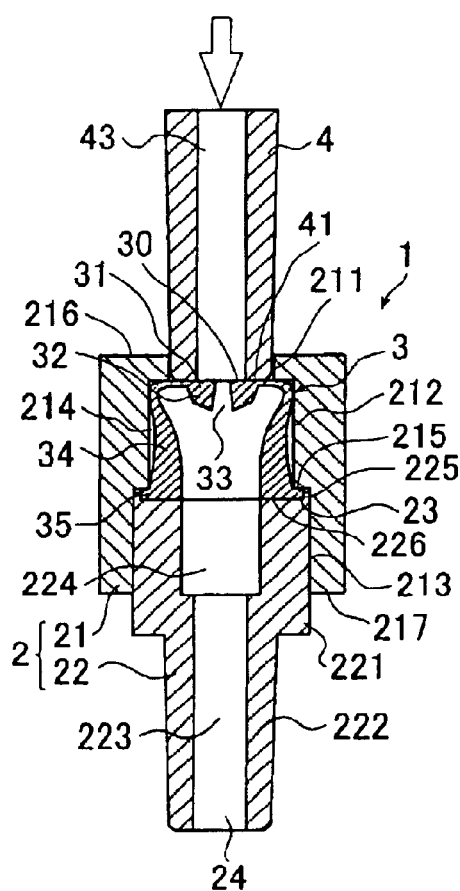
FIG. 5 is a longitudinal cross section of the connector of FIG. 1 and the tube when the distal end of the tube has been inserted into the connection port of the connector housing.

FIG. 5 shows the state when the tube 4 has moved further in the distal direction into the connector 1 and the distal end surface 41 of the tube 4 has entered the connection port 211 of the cylinder 21. When the tube is at this position, the base 34 has also been deformed by the pushing of the tube 4. As shown in FIG. 5, when the valve portion 30 of the valve 3 is further pushed by the distal end surface 41 of the tube 4, the valve portion 30 moves into the intermediate diameter space 212 and the base 34 of the valve 3 becomes compressed in its axial direction.

When the wall thickness (i.e. the flexural modulus) of the base 34 gradually decreases from the distal side to the proximal side of the base 34, it is the proximal side of the base 34 that mainly undergoes the deformation to become dilated in radially outward direction.

In the embodiment shown in FIG. 5, dilatation of the base 34 is restricted to a certain degree by the inner surface of the intermediate diameter space 212 of the cylinder 21, and the distal end of the base 34 can no longer dilate outward once it has dilated to the extent that the space 214 is barely left between the base 34 and the inner surface of the intermediate diameter space 212.

As described above, the base 34 becomes compressed in its axial direction and undergoes an elastic deformation to become dilated until it is restricted by the inner diameter of the intermediate diameter space 212, and the proximal surface 31 of the valve 3 is pushed down to the proximal end of the intermediate diameter space 212 of the cylinder 21. As a consequence, the slit 33 opens to a further degree with the fluid passage 43 of the tube 4 and the fluid passage 24 of the connector 1 becoming communicated with each other.

Figure 6:
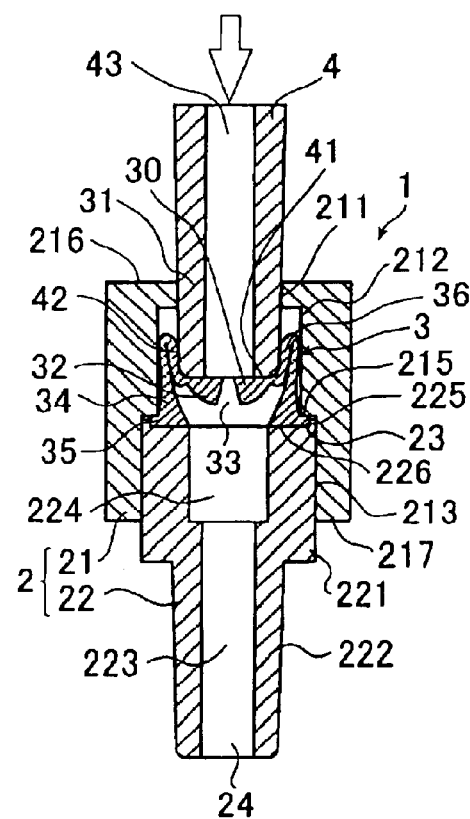
FIG. 6 is a longitudinal cross section of the connector of FIG. 1 and the tube after completing the engagement of the tube with the connector (when the distal end of the tube has entered into the intermediate diameter space of the connector housing).

When the tube 4 is further moved in distal direction for further insertion into the connector 1, there will occur the state of FIG. 6.

FIG. 6 shows the state when the tube 4 has finally engaged with the connector 1 with the distal end surface 41 of the tube 4 entering the intermediate diameter space 212 of the cylinder 21.

In this phase, when the tube 4 is further pushed inward in the distal direction from the state of FIG. 5 where the proximal surface 31 of the valve 3 had been located at the proximal end of the intermediate diameter space 212, the base 34 of the valve 3 becomes further compressed in the axial direction. The distal end portion of the base 34 having a lower flexural rigidity (namely, the part of the base 34 on the side of the valve portion 30) can no longer withstand the force of compression, and at this point, this part becomes bent (folded) in the radially inward direction. The folded portion 36 is thereby formed on the proximal side of the base 34.

Furthermore, in this phase, inner diameter of the inner cavity of the valve 3 has become larger than the outer diameter of the tube 4, and accordingly, a space (space which allows dilatation) is formed between the tube 4 and the base 34 of the valve 3. It is this space that is utilized for insertion of the folded portion 36, and the part (region) of the proximal end portion of the valve 3 that is in close contact with the tube 4 increases as this part is further pushed downward by the tube 4.

As a consequence, the part (region) in the valve portion 30 of the valve 3 that is in close contact with the tube 4 sinks into the interior of the base 34 of the valve 3 with the distal end of the tube 4 being wrapped by the folded portion 36. The distal peripheral surface 42 of the tube 4 also becomes in close contact with the folded portion 36, and the tube 4 is consequently in close contact with the valve 3 on both the distal end surface 41 and the distal peripheral surface 42.

As described above, the tube 4 is in close contact with the valve 3 not only at the distal end surface 41 but also at the distal peripheral surface 42 which is wrapped by the proximal surface 31 and the folded portion 36 of the valve 3. The contact area between the tube 4 and the valve 3 is thus increased with a remarkable improvement in the sealing capability (liquid tightness and gas tightness) between the tube 4 and the valve 3, and fluid leakage and other problems are reliably prevented.

In addition, unintentional disengagement of the tube 4 from the connector 1 is prevented since, as shown in FIG. 6, the tube 4 has fitted in the connection port 211 by the taper at the exact position where the outer diameter of the tube 4 coincides with the inner diameter (diameter of the opening) of the connection port 211, and at the same time, the distal end of the tube 4 has been wrapped around and reliably supported by the folded portion 36 of the valve 3 which has undergone the deformation.

As shown in FIG. 6, when the tube 4 is engaged with the connector 1 in the present invention, the distal end surface 41 and the distal peripheral surface 42 of the tube 4 do not penetrate through the valve 3 and intrude into the fluid passage of the housing 2, and therefore, there will not be the inconvenience that the slit 33 is forced open to an excessive degree to detract form the liquid tightness. In addition, even if the distal end surface 41 and the distal peripheral surface 42 of the tube 4 had some foreign matter (dirt, dust, and the like), bacteria, and the like attached thereto, intrusion of such matter into the housing 2, namely, contamination of the housing 2 is prevented.

When the tube 4 that had been in the state of FIG. 6 is withdrawn from the connector 1 by moving the tube 4 in the proximal direction, the valve 3 is liberated from the force of pushing by the tube 4, and the base 34 restores its original shape and length by the resilient restoration force of the valve 3. In such process, the proximal end of the valve 3 moves back into the connection port 211 of the cylinder 21, and the valve portion 30 of the valve 3 also restores its original shape with its first projection 31 protruding beyond the connection port 211 as shown in FIG. 1.

In addition, the slit 33 becomes closed again to recover its liquid tightness once the valve 3 has restored its original shape, and even if the fluid flew, for example, in reverse direction toward the proximal end after the disengagement of the tube 4 with the connector 1, the fluid is prevented from flowing out of the connector 1 from its proximal end.

When the slit 33 is formed in the thick region of the valve portion 30 where both the proximal surface 31 and the rear surface 32 are formed with the projection as in the case of the embodiment as described above, sealing capability of the slit 33 would be higher than the case where the slit is formed in a flat member of consistent thickness, and fluid leakage can be more reliably prevented against increase in the inner pressure of the housing 2 and the like.

In addition, since the connector 1 is not the type where the engagement of the tube 4 is accomplished by penetration of the tube 4 through the slit 33 of the valve 3 as described above, the slit 33 is not forced open to an excessive degree, and the sealing capability of the slit 33 of the valve 3 remains substantially undamaged even after frequent engagement and disengagement of the tube 4 with the connector 1.

In the foregoing, the connector of the present invention has been described by referring to one embodiment shown in the drawings. The present invention, however, is not limited to such embodiment, and the connector may comprise components having various constitutions. In particular, the valve and the housing may have various shapes and mechanisms, and they can be modified as long as equivalent functions are achieved. Examples of such modification for the embodiment as described above are given below.

1. In the embodiment as described above, the cylinder 21 of the housing has been described for the shape and the structure that enable engagement of the cylinder 21 with the tube 4. The cylinder 21, however, may also have the shape and the structure that enable engagement with Luer taper or Luer lock.

In the embodiment as described above, the connector has also been described for the case wherein a single tube was connected with another tube. The housing provided on the remote side to the connector, however, is not limited for its shape and number of Branches. Exemplary shapes include the shapes of branched (Y) connector, T connector, J loop, and PRN adapter.

2. In the embodiment as described above, the valve 3 and the housing 2 were formed from separate members. However, the valve 3 and the cylinder 21, or the valve 3 and the cap 22 may be formed as one integral part by coinjection molding, insert molding, or the like. The number of the parts can then be reduced.

3. The slit 33 is not limited to the straight shape as shown in the drawings, and it may be formed, for example, in the shape of cross, L, H, U, and the like. When adjustment of the flow rate is required in some applications, two or more slits may be formed as the slit 33.

4. In the embodiment as described above, the base 34 of the valve 3 has been described for case wherein the base 34 has been formed in a cylindrical shape. The base 34 may also have a pleated section with the function of a spring to thereby facilitate restoration of its original shape.
5. Although it might be needless to say, the flange 35 is not limited to the shape shown in the drawings, and it may take different shapes as long as it enables reliable fixture of the valve 3 to the housing 2.
6. The inner cavity of the base 34 of the valve 3 can also be formed in a configuration other than the columnar, conical, or other shapes which are formed by rotating an unchanging region about the axis of revolution.

Next, several other embodiments of the present invention are described by referring to the drawings. With regard to these drawings, description has been partly omitted to avoid redundancy. However, the numerals which are the same as those of FIGS. 1 to 6 designate the same members as those of FIGS. 1 to 6. Some embodiments have been described by using simplified drawings where some numerals have been abbreviated.

For example, with regard to the housing 2 (the cylinder 21) of the connector 1, there is shown an embodiment wherein the space 214 remains in the intermediate diameter space 212 even after the engagement of the tube 4 and dilatation of the base 34 of the valve 3.

FIG. 7A is a view corresponding to FIG. 1 wherein the tube 4 is not yet engaged with the connector 1 having such structure, and FIG. 7B is a view corresponding to FIG. 6 showing the state when the tube 4 has been engaged with the connector 1. As shown in FIG. 7B, the space 214 has remained between the valve 3 and the inner surface of the housing even after the formation of the folded portion 36 in the valve 3 by the pushing of the valve 3 with the tube 4 and the dilatation of the base 34. Such elastic deformation of the valve 3 with the remaining space 214 is preferable since the base 34 does not receive the stress from the housing 2 (cylinder 21). The force of pushing by the tube 4 will than be equally distributed and the valve is better prepared for the fluctuation of the inner pressure.

FIG. 8 shows an embodiment wherein the valve portion 30 of the valve 3 has been formed to a different shape. In this embodiment, two projections 31a and 31a are formed on opposite sides of the slit 33, and a recess 31b is formed in the central region of the proximal surface 31 between the two projections. A project is also formed on the rear surface 32 of the valve portion 30, and the slit 33 is located along the summit of this projection.

FIG. 8 is also an embodiment wherein the connector is formed with the space 214 similar to that of FIG. 7 while the space 224 formed in the distal portion 222 of the cap 22 has an inner diameter larger than that of the distal end portion of the inner cavity in the valve 3. In the embodiment of FIG. 8, the space 224 serves a relief space for the part of the valve 3 which sinks into this space upon engagement of the tube 4. When a part of the valve 3 sinks into the relief space as in the case of this embodiment, it is preferable to secure the valve 3 with a higher reliability, for example, by providing the flange 35 of the valve 3 with a leg 35a. In such a case, the valve-supporting area 226 of the housing 2 should also have the corresponding shape so that the leg 35a can be sandwiched within the valve-supporting area 226.

Figure 8A:
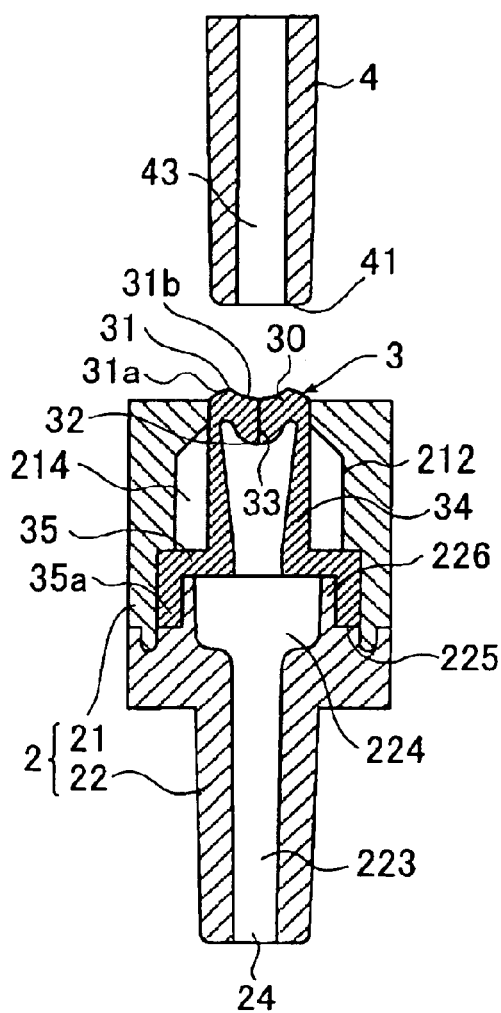
FIG. 8 is a longitudinal cross section of a connector according to another embodiment of the present invention.
Figure 8B:
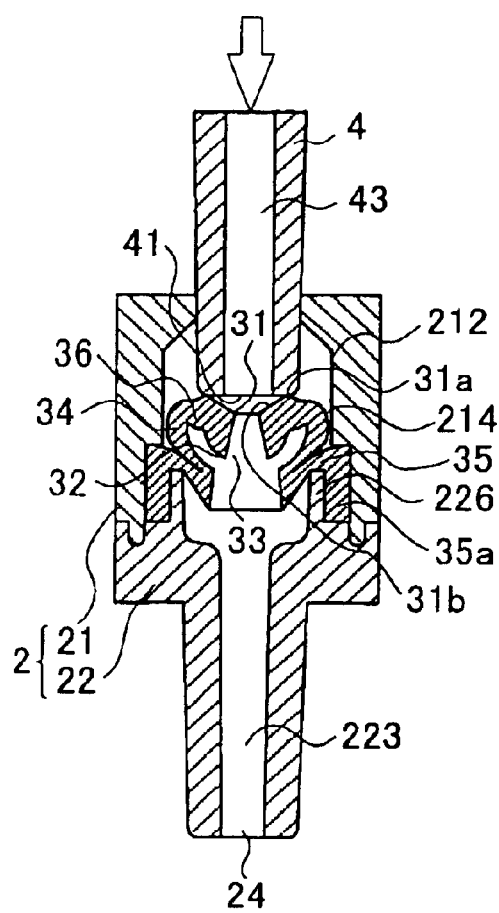

FIG. 8A is a view corresponding to FIG. 1 wherein the tube is not yet engaged with the connector 1 having such structure. FIG. 8B is a view corresponding to FIG. 6 wherein the tube 4 has been engaged with the connector 1.

When the valve portion 30 is provided on its proximal surface 31 with the projections 31a and 31a and the recess 31b, and the tube 4 presses the valve 3 into the intermediate diameter space 212 for engagement (FIG. 8B), the tube 4 will be supported by the projections 31a and 31a formed on the proximal surface 31 with no contact occurring between the distal end surface 41 (preferably the opening of the fluid passage 34) and the recess 31b formed on the proximal surface 31.

Reliable engagement and disengagement of the tube 4 is also enabled since the valve 3 pushed by the tube 4 becomes dilated in the intermediate diameter space 212 leaving the space 214, and some part of the valve 3 sinks into the relief space 224 as shown in FIG. 8B, and the valve 3 enjoys high freedom of disposition/deformation. In addition, the valve 3 does not experience a drastic change in the volume of the inner cavity, and pressure change in the valve 3 is limited to a small degree. As a consequence, the connector is avoided from experiencing the "leakage" upon disengagement of the tube 4 from the connector.

Next, another embodiment of the connector is described for its detailed structure by referring to FIGS. 9 to 14. This connector has an inner structure similar to that of FIG. 8, and this connector is also provided on the proximal and distal ends of its housing with spiral screw threads (Luer lock threads) to enable screw engagement with the tubes. The numerals which are the same as those of FIGS. 1 to 8 designate the same parts as those of FIGS. 1 to 8, and redundant explanation has been omitted.

FIG. 9 is a plan view of the connector 1 seen from the proximal end. The valve 3 is formed with the two projections 31a and 31a and the recess 31b in the center as in the case of FIG. 8, and this valve is inserted in the connection port 211 on the proximal end 216 of the housing 2 (cylinder 21). A slit 33 is formed in the recess 31b of the valve 3. FIG. 10 is a longitudinal cross section of the connector 1 and the tube 4 taken along slit 33 (line X—X) of FIG. 9, and FIG. 11 is a longitudinal cross section of the connector and the tube taken along line XI—XI.

Figure 11:
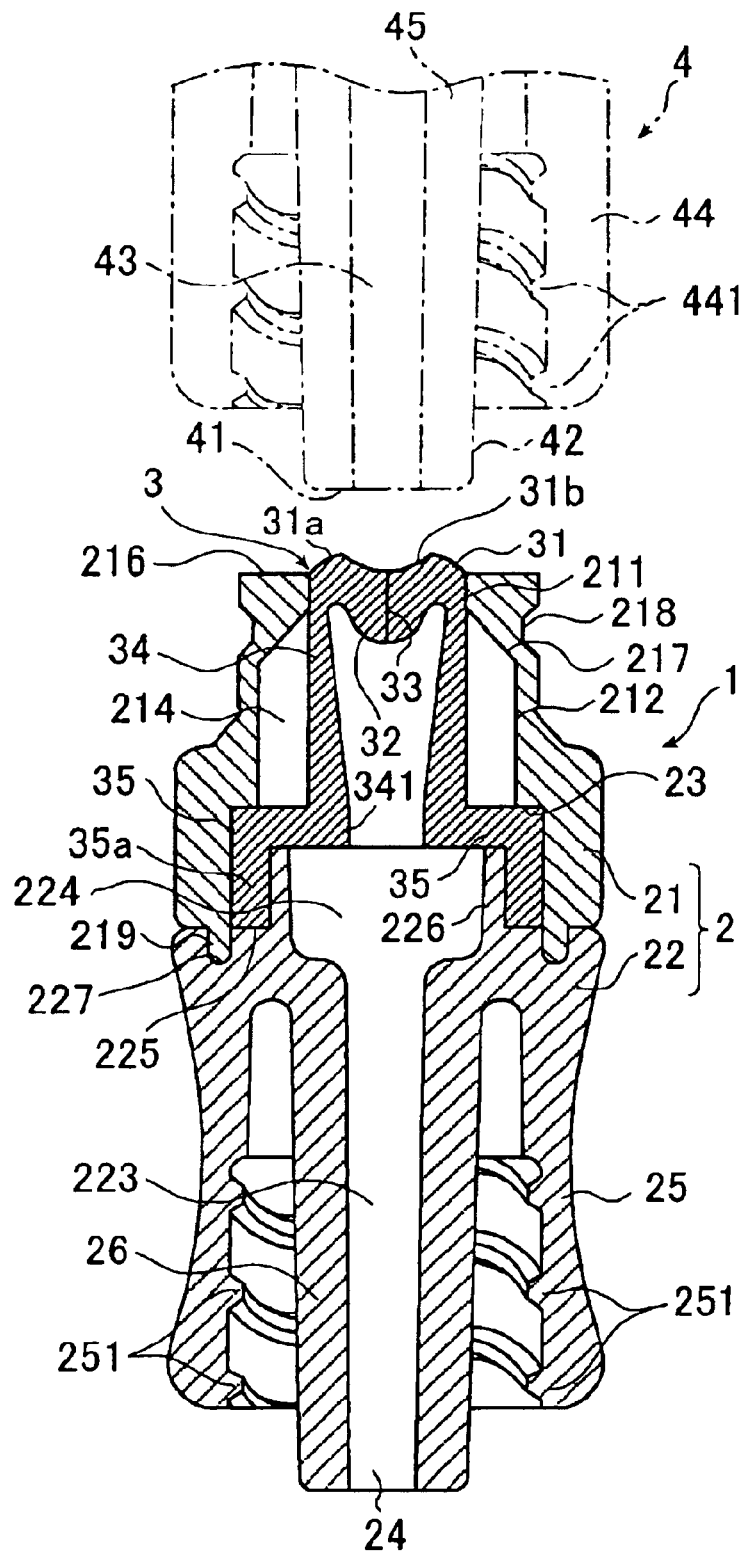
FIG. 11 is a longitudinal cross section of the connector of FIG. 10 taken along the line XI—XI.

As shown in FIGS. 10 and 11, the cap 22 of the housing 2 has a double tube structure comprising an inner cylinder 26 and a sleeve 25 provided with Luer lock threads 251 on its inner surface. This inner cylinder 26 corresponds to the distal portion 222 of FIG. 1 wherein the cap has a single tube structure. A Luer taper is formed on the outer surface of the inner cylinder 26 to facilitate direct engagement with a tube (not shown) or engagement with the tube with an intervening connecting device (not shown) so that the fluid passage 24 of the connector would be in liquid tight communication with the inner cavity of such tube or connecting device. Alternatively, the inner cylinder 26 may have a constant outer diameter. The distal end of the inner cylinder 26 generally extends beyond the distal end of the sleeve 25. This inner cylinder 26 has an interior structure which is substantially the same as that of the embodiment shown in FIG. 8, and the spaces 223 and 224 are provided in the interior. As described above, the space 224 on the proximal side serves the relief space for the valve 3 in the engagement of the tube 4.

In the embodiment shown in FIG. 10, the cap 22 and the cylinder 21 are engaged with each other by the fitting of an annular projection 219 provided on the cylinder 21 concentrically with said groove 226 in the groove 227 provided on the distal end 225 of the cap 22. As described above, the means of connecting the cap 22 and the cylinder 21 is not limited to any particular means.

The cylinder 21 also has a structure similar to that of the embodiment shown in FIG. 8 except that a guide taper 217 is formed in the interior of the proximal side of the cylinder 21 between the connection port 211 and the intermediate diameter space, and the cylinder is provided on its outer surface with Luer lock threads 218.

In the embodiment of FIGS. 10 to 11, when the base 34 of the valve 3 has an average outer diameter of $D_1$, and the relief space 224 has an average inner diameter of $D_2$, the ratio of the average inner diameter of $D_2$ of the relief space 224 to the average outer diameter $D_1$ of the base 34, namely, $D_2/D_1$ is preferably in the range of 0.5 to 2, and more preferably in the range of 1 to 1.2 although the ratio is not particularly limited.

The relief space 224 is not particularly limited for its depth $L_1$ (FIG. 11). The depth $L_1$, however, is preferably up to 5 mm, and more preferably in the range of 1 mm to 3 mm.

The base 34 of the valve 3 may have an outer diameter which is approximately the same or slightly larger the inner diameter of the cap-securing area 213 of the cylinder 21.

When the flange 35 (leg 35a) of the valve 3 has an average outer diameter of $D_3$, the ratio of the average outer diameter $D_3$ of the flange 35 to the average outer diameter $D_1$ of the base 34, namely, $D_3/D_1$ is preferably in the range of 1.2 to 2.5, and more preferably in the range of 1.8 to 2.2 although the ratio is not particularly limited. The valve 3 is reliably (and to be more specific, liquid tightly) secured to the housing 2 since the valve 3 has such flange 35 (leg 35a), and the leg 35a is sandwiched between the valve-supporting area 226 and the cap-securing area 213 of the housing 2.

As shown in FIG. 11, the base 34 of the valve 3 is tapered except for the part around the valve portion 30, and the wall thickness gradually increases toward the fixture portion 341. Such taper is not provided all around the inner peripheral surface of the base 34, and as shown in the cross section of FIG. 10, the base 34 is not tapered in this cross section. To be more specific, the base 34 has a constant wall thickness at the position where the wall is parallel to the slit 3 (FIG. 10) while the wall is tapered at the position where the wall is perpendicular to the slit 3 (FIG. 11). The base 34 is tapered around approximately half of the periphery, and sufficient strength and stability has been enabled by such constitution. Compared to the case wherein the base 34 is tapered all around its periphery, it is easier upon deformation of the valve 3 to maintain the fluid passage 24 (to be more specific, the area near the fixture portion 341) at a sufficient level, to reduce the fluctuation in the inner volume, and to maintain the inner pressure at a constant level. In addition, provision of the partially tapered area at the position as described above in relation to the slit 33 has enabled smooth opening and closure of the slit 33 as well as opening of the slit 33 by slight pushing force. The bending of the base 34 is also facilitated, and the base 34 reliably restores its original shape upon disengagement of the tube 4.

On the other hand, the base 34 of the valve 3 may preferably have a substantially constant outer diameter along its axis, and the taper is preferably provided on the inner surface. As a result of such configuration, increase in the outer diameter of the base 34 upon dilatation of the base 34 is limited to a certain extent, and increase in the diameter of the cylinder 21 can be avoided.

The tube 4 to be engaged with such connector 1 has a double tube structure comprising an inner tube 45 which is defined in its interior with the fluid passage 43, and a sleeve 44 which is provided on its interior with threads 441 to be screwed onto the Luer lock thread 218 of the connector 1. The inner tube 45 corresponds to the tube 4 in the single tube structure, described by referring to FIGS. 1 to 8. The distal end of the inner tube 45 generally extends beyond the distal end of the sleeve 44. The outer diameter of the inner tube 45 has Luer taper in the embodiment shown in the drawings. The inner tube 45, however, may also have a constant outer diameter.

Figure 12:
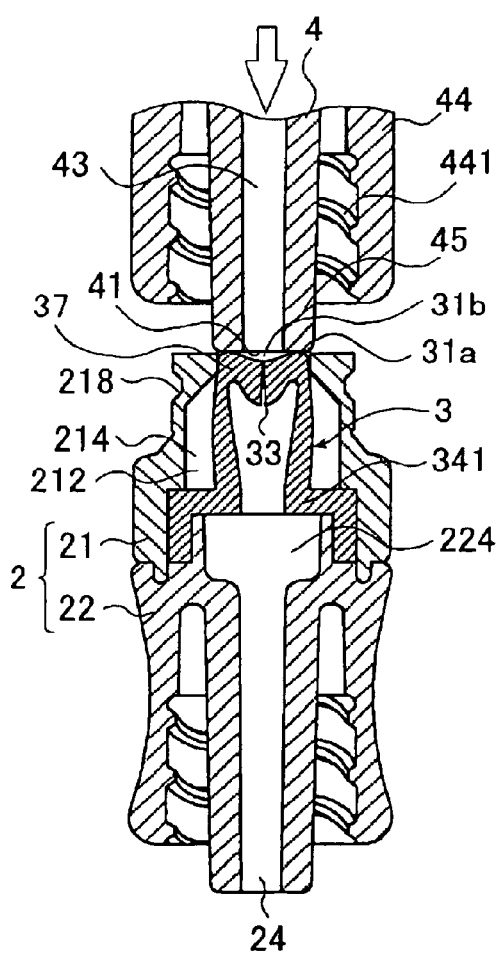
FIG. 12 is a longitudinal cross section of the connector according to the embodiment of FIG. 11 when the distal end surface of the tube was positioned on the connector.
Figure 13:
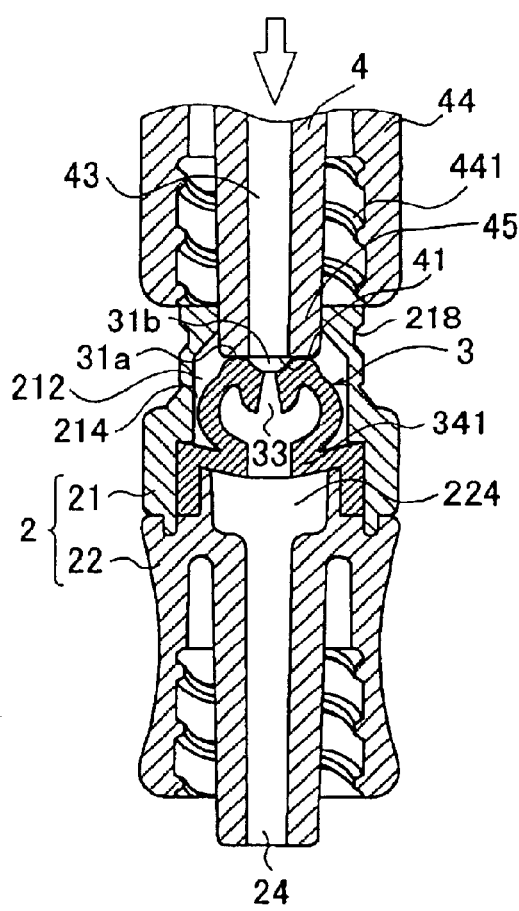
FIG. 13 is a longitudinal cross section of the connector according to the embodiment of of FIG. 11 when the distal end of the tube was inserted into the connection port of the cylinder.
Figure 14:
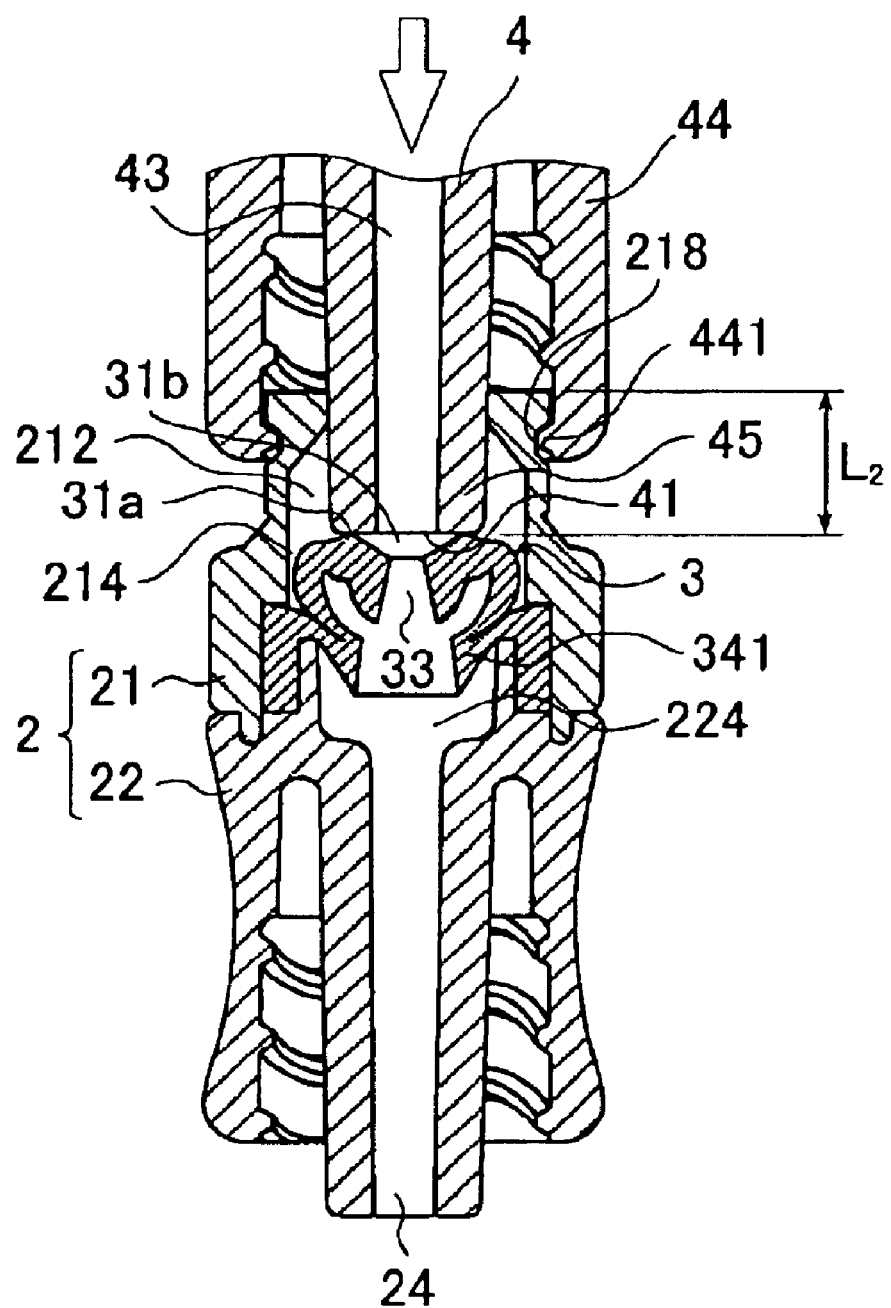
FIG. 14 is a longitudinal cross section of the connector according to the embodiment of of FIG. 11 after completing the engagement of the tube to the connector (when the distal end of the tube has entered into the intermediate diameter space of the connector housing).
Figure 15:
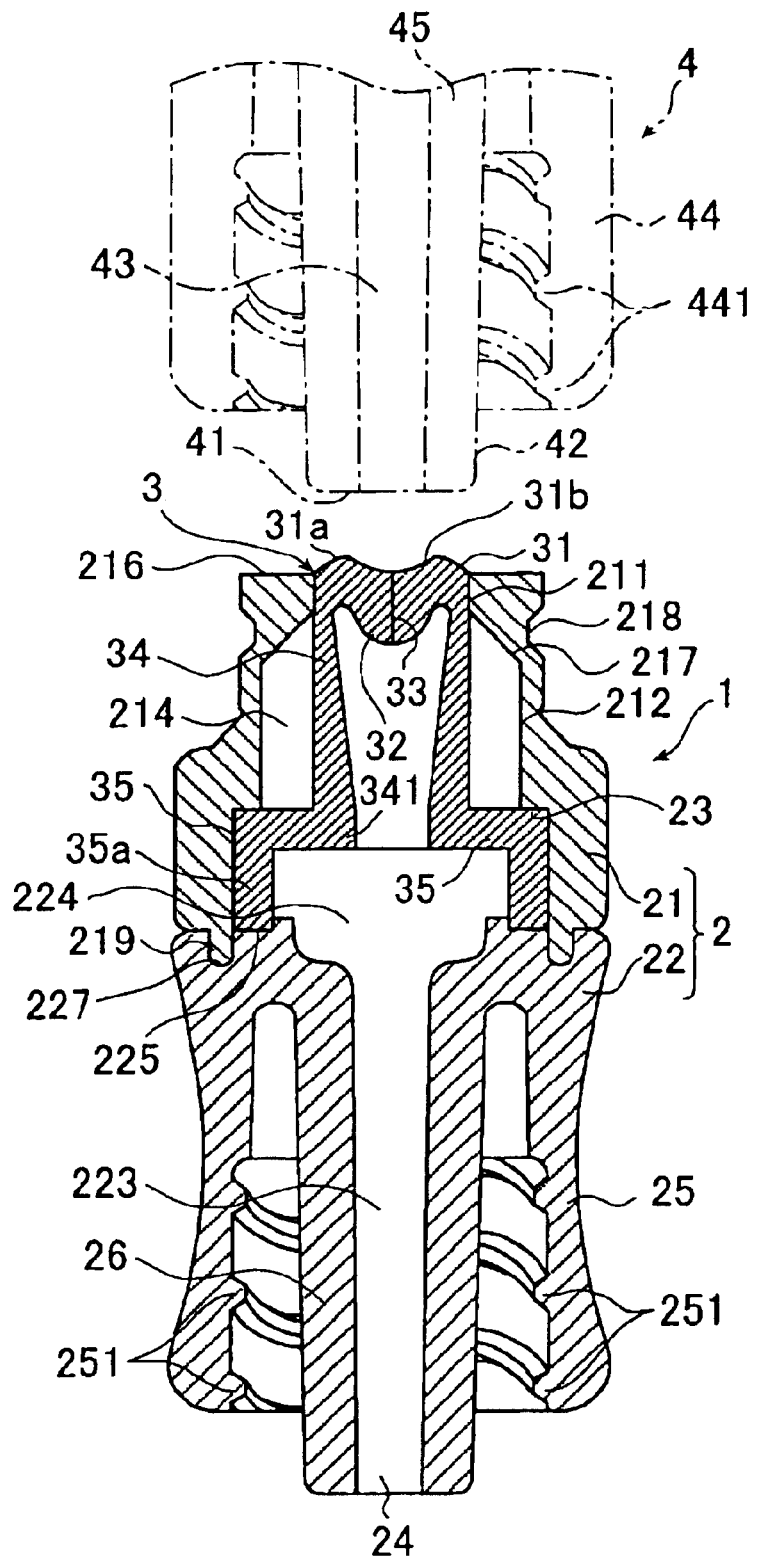

FIGS. 12 to 14 are schematic views illustrating the mechanism of engagement between the tube 4 and the connector 1. In these drawings, the numerals which are the same as those of FIG. 11 designate the same parts, and some numerals have been omitted. The connector 1 shown in FIGS. 12 to 14 has an interior structure which can be described in a substantially same way as the connector 1 of FIGS. 8A and 8B except that the housing 2 and the tube 4 have double tube structure.

Referring to FIG. 12, when the projections 31a and 31a on the valve portion 30 (the proximal surface 31) of the valve 3 are pushed by the distal end surface 41 of the tube 4, the valve becomes compressed in axial direction and the area of the base 34 near the valve portion 30 becomes slightly dilated. The central region of the valve portion 30 also moves slightly in distal direction, and the angle between the valve portion 30 and the base 34 becomes reduced. As a result, the distal end of the slit 33 on the side of the rear surface 32 becomes slightly opened. In the course of such process, the valve portion 30 undergoes deformation by the mechanism resembling that of the lever wherein the effort is applied to the projection 31a, the corner 37 serves the fulcrum, and the center of the recess 31b acts as the point of resistance. As a result of such action, displacement in the distal direction of the center of the recess 31b becomes larger than the displacement in distal direction of the projection 31a, and this results in the increase in the angle of opening of the slit 33 on the side of the rear surface 32. At this point, however, the slit 33 on the proximal surface 31 accommodated in the connection port 211 is not yet open.

FIG. 13 is a view when the tube 4 has been moved further in distal direction to be inserted in the connector 1, and the distal end of the sleeve 44 of the tube 4 has substantially reached the level of the proximal end 216 of the connector 1.

When the tube 4 is at this position, the valve portion 30 of the valve 3 has already been pushed into the intermediate diameter space 212 by the tube 4, and the valve portion 30 has been liberated from the constriction of the connection port 211 to become capable of being dilated in radially outward direction. The valve 3 has been compressed in axial direction, and the base 34 has been dilated into the "barrel shape". The thus deformed base 34 has acted to pull the valve portion 30 in radially outward direction. By this action, the valve portion 30 has become dilated in radially outward direction, and the slit 33 has become open along its full depth so that the fluid passage 24 of the connector 1 has become in communication with the fluid passage 43 of the tube 4. At this stage, the fixture portion 341 of the valve 3 has sunk slightly into the relief space 224 with the space 214 maintained at a sufficient level.

FIG. 14 shows the state (state of engagement) wherein the Luer lock threads 441 have been screwed onto the Luer lock screw 218 by rotating the tube 4 from the state of FIG. 13. In the thus engaged state, the inner tube 45 of the tube 4 has been fitted in the connection port 211 of the connector 1 with the tube 4 being reliably engaged with the connector 1. In addition, the distal end surface 41 of the tube 4 has reached approximately to the middle of the intermediate diameter space 212. As a result, the valve 3 has undergone a substantial compression in axial direction to about half its length before the engagement.

The slit 33 is now fully open, and the fluid passage 24 is in full communication with the fluid passage 43 of the tube 4. The space 214 is maintained.

The fixture portion 341 of the valve 3 has sunk into the relief space 224 together with the part of the flange 35 near the fixture portion 341. Since such substantial deformation is enabled by the provision of the relief space 224, the tube 4 can be engaged even if the length (FIG. 14, $L_2$) of the tube 4 (inner 45) to be inserted in the connector were different, for example, even if the $L_2$ were longer. Accordingly, the connector 1 has enabled engagement of the tubes 4 having different insertion length.

In particular, a longer insertion length $L_2$ is required when the connector 1 and the tube 4 are engaged with each other by screwing with Luer lock threads as in the case of the present embodiment. The present invention, however, has enabled reliable action of the valve 3 and reliable opening and closure of the slit 33 upon engagement and disengagement of the tube 4.

The fixture portion 341 and some part of the flange 35 of the base 34 can sink into the relief space 224, and therefore, the base 34 and the valve portion 30 enjoy high degree of deformation freedom, and it is the presence of the space 214 that has increased such degree of freedom. A reliable opening of the slit 33 to a large opening area is thereby enabled. Furthermore, the inner volume of the valve 3 does not fluctuate to an excessive degree during the engagement and the disengagement, and fluid leakage due to the fluctuation in the inner pressure is unlikely to occur upon disengagement of the tube 4.

As described above, the present invention does not function by the connector engaging/disengaging mechanism wherein engagement of the tube 4 to the connector 1 is accomplished by the penetration of the distal end surface 41 and the distal peripheral surface 42 of the tube 4 through the valve 3 and their intrusion into the fluid passage 24 in the housing 2. Therefore, the present invention is free from the inconvenience that the slit 33 is forced open to an excessive degree to detract form the liquid tightness. In addition, even if the distal end surface 41 and the distal peripheral surface 42 of the tube 4 had some foreign matter (dirt, dust, and the like), bacteria, or the like attached thereto, intrusion of such matter into the housing 2, namely, contamination of the housing 2 is prevented.

When the tube 4 is unlocked by rotating the tube 4 in the direction opposite to the one used in the engagement and withdrawn from the connector 1 from the engaged state shown in FIG. 14 by moving the tube 4 in the proximal direction, the valve 3 is liberated from the force of pushing by the tube 4, and the base 34 restores its original shape and length by the resilient restoration force of the valve 3. In such process, the valve portion 30 of the valve 3 restores its original shape and enters the connection port 211 as it is guided by the guide taper 217, and the projection 31a protrudes beyond the proximal end 216 of the housing 2 as shown in FIG. 11.

In addition, the slit 33 becomes closed again to recover its liquid tightness once the valve 3 has restored its original shape, and even if the fluid flew, for example, in reverse direction toward the proximal end after the disengagement of the tube 4 with the connector 1, the fluid is prevented from flowing out (fluid leakage) of the connector 1 from its proximal end. When the slit 33 is formed in the thickened valve portion 30 of the valve 3 as in the case of the embodiment as described above, sealing capability of the slit 33 would be higher than the case where the slit is formed in a flat area, and fluid leakage can be more reliably prevented against increase in the inner pressure of the housing 2 and the like.

In addition, since the connector 1 is not the type wherein the tube 4 is engaged by penetration of the tube 4 through the slit 33 of the valve 3 as described above, the slit 33 is not forced open to an excessive degree, and the sealing capability of the slit 33 of the valve 3 remains substantially undamaged even after frequent engagement and disengagement of the tube 4 with the connector 1.

The embodiments as described above may be modified in various ways. In one typical such modification, the valve-supporting area 226 of the cap 22 is formed to extend substantially to the level of the distal end 225 so that it does not extend as far as FIG. 11.

Figure 16A:
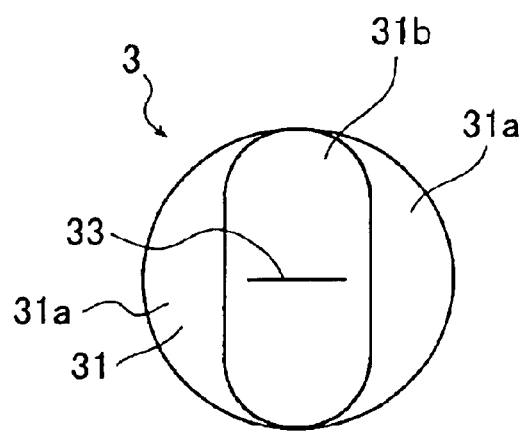
FIG. 16 is a plan view showing another embodiments of the valve.
Figure 16B:
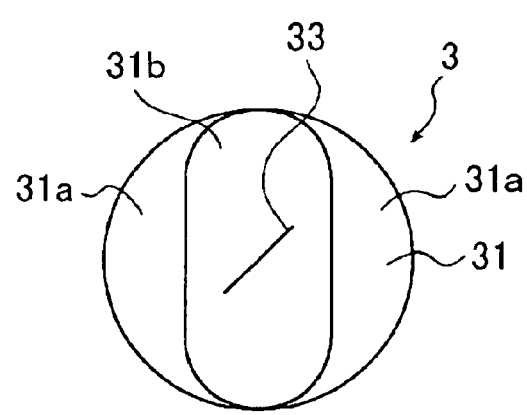

FIG. 16 shows embodiments wherein the slit 33 has been formed in different directions. The slit 33 has been described in FIG. 9 for the embodiment wherein a straight slit has been formed in the ellipsoidal recess 31b in its longitudinal direction. The slit 33, however, may be formed in the direction crossing such longitudinal direction (FIG. 16A) or in the direction diagonal to the axial direction (FIG. 16B). As described above, the slit is not limited to the straight shape.

Figure 17A:
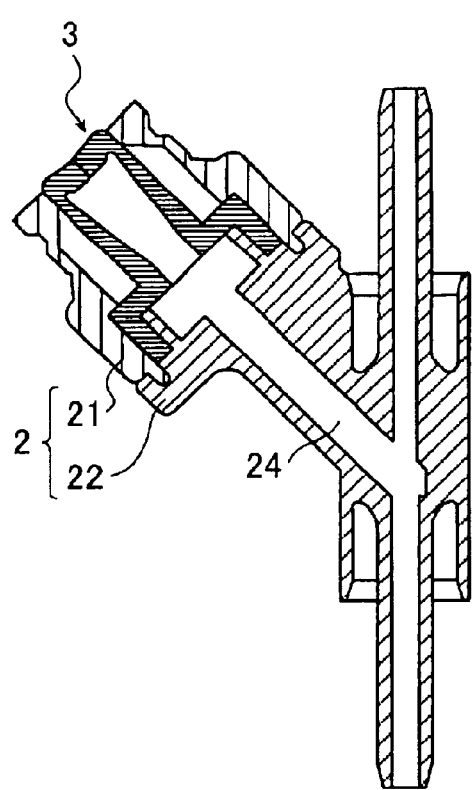
FIG. 17 is a longitudinal cross section showing embodiments of Y housing connector.
Figure 17B:
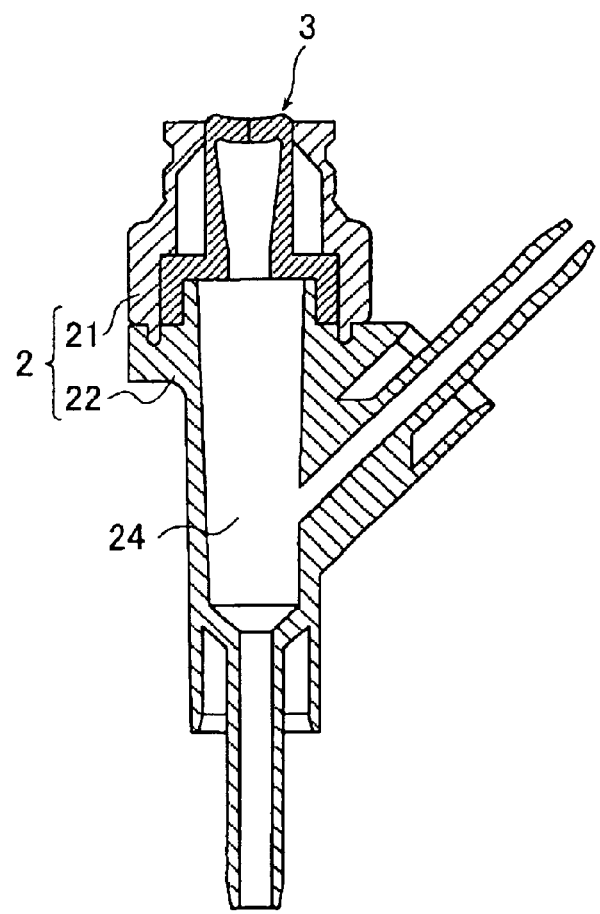

FIG. 17 shows embodiments wherein the housing is branched. In FIGS. 17A and 17B, there are respectively depicted embodiments wherein the connector of FIG. 11 has a cap 22 in Y shape.

Figure 18:
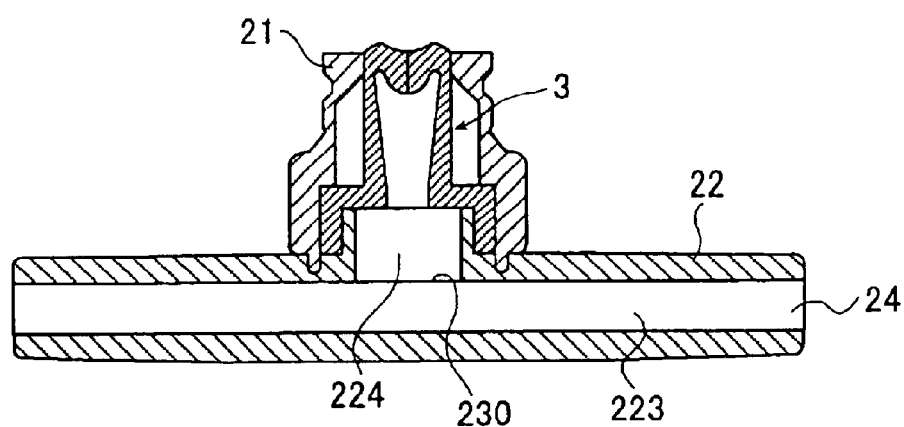
FIG. 18 is a longitudinal cross section showing an embodiment of T housing connector.

FIG. 18 shows a modification of FIG. 11 wherein the cap 22 has been modified such that the connector 1 is a T connector. The connector 1 has a structure similar to that of FIG. 11 except that the tube (cap) 22 is provided on its side surface with an opening 230, and the space 224 of the cylinder 21 and the fluid passage 223 are arranged in the direction perpendicular to the axial direction of the cylinder 21 to define the fluid passage 24.

Figure 19:
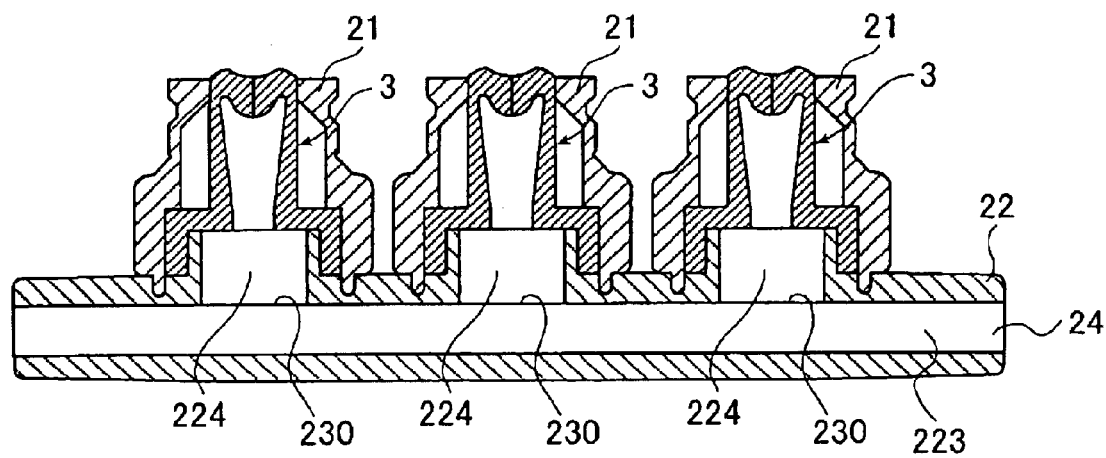
FIG. 19 is a longitudinal cross section showing an embodiment wherein a plurality of connectors are aligned in parallel.

FIG. 19 shows an embodiment wherein a plurality of connectors 1 are arranged along one fluid passage 24. In this embodiment, the tube (cap) 22 is provided on its side surface with, for example, three openings 230, and the cylinders 21 which are similar to the one shown in FIG. 18 are arranged at each opening.

Next, the present invention is described in further detail by referring to the Examples which by no means limit the scope of the present invention.

EXAMPLE 1

The connector 1 of FIGS. 1 and 2 as described above was applied for a part of the Y site serving the infusion inlet port of a medical infusion set.

The valve 3 having the shape as shown in FIGS. 1 and 2 was manufactured from a silicone rubber, and a straight slit 33 as shown in FIG. 2 was formed to penetrate through the central region of the valve portion 30 of the valve 3. The slit 33 was formed to a length of 2 mm on the side shown in FIG. 2 considering the inner diameter and the length of the syringe (tube 4). The central region (thick region) of the valve portion 30 in the valve 3 had a maximum thickness of 2.2 mm, and the valve 3 had a height (full length) of 7.6 mm. The base 34 had a thickness at the proximal end of 0.5 mm (minimum) and a thickness at the distal end of 2 mm (maximum) with the thickness gradually increasing toward the distal end.

The cylinder 21 and the cap 22 having the shapes as shown in FIGS. 1 and 2 were injection molded from polycarbonate, respectively. The inner diameters of the connection port 211, the intermediate diameter space 212, and the large diameter cap-securing area 213 of the housing 2 were 4 mm, 6.2 mm, and 8 mm, respectively.

The valve 3 was mounted in the cylinder 21, and the cap 22 was then fitted in the cylinder 21 with caulking. The cap 22 and the cylinder 21 were fixedly secured by ultrasonic fusion. The valve 3 became reliably secured to the housing 2 by the sandwiching of the flange 35 between the cap 22 and the cylinder 21.

When distal tip (Luer taper, needle unattached) of a syringe was inserted in the connection port 211 of the connector 1 which had been assembled as described above, the valve 3 underwent the elastic deformation as shown in FIG. 6 as the distal end surface 41 pushed the valve portion 30 of the valve 3. The valve portion 30 sank into the connection port 211 of the connector 1, and the relatively thin part of the base 34 near the valve portion 30 became folded, and as a consequence, the distal end surface 41 and the distal peripheral surface 42 of the distal tip of the syringe became wrapped around by the folded portion 36.

Even if the distal peripheral surface 42 of the syringe distal tip and other parts were contaminated with bacteria or the like that had fallen on the surface, it was enabled by such structure to reduce the danger of direct intrusion of the bacteria into the infusion passage of the connector 1.

After introducing the infusion through the syringe, the syringe was withdrawn from the connector 1. The valve 3 then restored its original shape, and the slit 33 became reliably closed to regain its liquid tightness.

Next, the valve 3 was evaluated for air leakage by the test procedure as described below. The connector 1 was placed in water, and compressed air was gradually supplied to the housing 2 of the connector 1 with the slit 33 of the valve 3 closed to thereby increase the pressure in the housing 2. The air leakage was not observed until the pressure in the housing 2 reached 0.38 MPa.

Next, the distal tip of the syringe was repeatedly engaged and disengaged with the connector 1 for 200 times as described above, and the connector 1 was evaluated for the air leakage by the test procedure similar to the one as described above. The air leakage occurred when the pressure reached 0.38 MPa, and it was then confirmed that the valve 3 experienced substantially no decrease in its the sealing capability (liquid and gas tightness).

EXAMPLE 2

The connector 1 of FIGS. 9 to 11 as described above was applied for a part of the Y site serving the an infusion inlet port of a medical infusion set.

The valve 3 having the shape as shown in FIGS. 9 to 11 was manufactured from a silicone rubber, and a straight slit 33 as shown in FIG. 9 was formed to penetrate through the central region of the valve portion 30 of the valve 3. The slit 33 was formed to a length of 2 mm on the side shown in FIG. 9 considering the inner diameter and the length of the syringe (tube 4).

The thickness of the central region (thick region) of the valve portion 30 in the valve 3 was 1.2 mm at the thinnest position, namely, at the site where the recess 31a was formed on the proximal end surface 31, and 1.8 mm at the thickest position, namely, at the site where the top of the projection on the rear side 32 was located. The valve 3 had a height (full length) of 9.4 mm. The base 34 had an outer diameter $D_1$ of 4.0 mm, and the flange 35 (leg 35a) had an outer diameter $D_3$ of 8.0 mm.

The base 34 had a thickness at the proximal end of 0.5 mm (minimum) and a thickness at the distal end of 1.0 mm (maximum) with the thickness gradually increasing toward the distal end. The base 34 in the cross section of FIG. 10 had a thickness of 0.6 mm which was constant in the axial direction.

The cylinder 21 and the cap 22 having the shapes as shown in FIGS. 10 and 11 were injection molded from polypropylene, respectively. The inner diameters of the connection port 211, the intermediate diameter space 212, and the cap-securing (large diameter) area 213 of the housing 2 were 4.0 mm, 6.2 mm, and 8 mm, respectively. The relief space 224 had an inner diameter $D_2$ of 5.0 mm.

The valve 3 was mounted in the cylinder 21, and the cap 22 was then fitted in the cylinder 21 with caulking. The cap 22 and the cylinder 21 were fixedly secured by ultrasonic fusion. The valve 3 became reliably secured to the housing 2 by the sandwiching of the flange 35 between the inner surface of the cylinder 21 and the valve-supporting area 226.

When distal tip (Luer taper, needle unattached) of a syringe was inserted in the connection port 211 of the connector 1 which had been assembled as described above, the valve 3 underwent the elastic deformation as shown in FIG. 14 as the distal end surface 41 pushed the valve portion 30 of the valve 3.

Even if the distal peripheral surface 42 of the syringe distal tip and other parts were contaminated with bacteria or the like that had fallen on the surface, it was enabled by such structure to reduce the danger of direct intrusion of the bacteria into the infusion passage of the connector 1.

After introducing the infusion through the syringe, the syringe was withdrawn from the connector 1. The valve 3 then restored its original shape, and the slit 33 became reliably closed to regain its liquid tightness.

Next, the valve 3 was evaluated for the air leakage by repeating the test procedure of Example 1.

The connector 1 was placed in water, and compressed air was gradually supplied to the housing 2 of the connector 1 with the slit 33 of the valve 3 closed to thereby increase the pressure in the housing 2. The air leakage was not observed until the pressure in the housing 2 reached 0.38 MPa. Next, the distal tip of the syringe was repeatedly engaged and disengaged with the connector 1 for 200 times as described above, and the connector 1 was evaluated for the air leakage by the test procedure similar to the one as described above. The air leakage occurred when the pressure reached 0.38 MPa, and it was then confirmed that the valve 3 experienced substantially no decrease in its the sealing capability (liquid and gas tightness).

INDUSTRIAL APPLICABILITY

As described above, the present invention has enabled to prevent intrusion of the foreign matters, bacteria, and the like attached on the distal end of the tube to the interior of the connector since the connector of the present invention is not the type wherein the engagement is attained by penetration of the tube through the connector valve.

A high sealing capability, and hence, a reliable prevention of the fluid leakage is also achieved since not only the distal end surface but also the distal peripheral surface becomes in close contact with the valve once the tube is engaged with the connector. In particular, leakage from the interface between the tube and the valve upon increase in the connector inner pressure is prevented.

The tube is also in reliable engagement with the connector, and unintended disengagement of the tube from the connector is thereby prevented.

Furthermore, the slit is reliably closed after the disengagement of the tube from the connector, and leakage of the fluid from the connector through the valve is prevented even if the fluid flew in reverse direction.

What is claimed is:

1. A connector comprising:

a housing provided with a fluid passage in its interior and a connection port for engagement with a tube; and a valve of an elastic material accommodated in said housing; wherein said valve has a cylindrical base which is tapered such that a wall thickness gradually increases toward a distal end; a valve portion on one axial end of said base which becomes in contact with said tube to be pushed inward by said tube; and a slit formed in said valve portion which opens when said valve portion is pushed inward, wherein the slit has a size such that said tube cannot penetrate through the slit upon opening of said slit; and said valve undergoes elastic deformation when said tube is engaged with said connection port of the housing by pushing said tube against said valve portion of the valve, and said slit opens as a result of said elastic deformation, and a base of which the wall thickness gradually increases toward the distal end causes a larger deformation on a proximal side than a distal side because of lower flexural strength on the proximal side, such that said valve portion becomes in close contact with distal end surface and distal peripheral surface of said tube.

2. A connector according to claim 1, said tapered base in which the wall thickness gradually increases toward the distal end becomes folded such that said valve portion enters the interior of said base and a new interior surface defined by the folded valve portion becomes in close contact with distal peripheral surface of said tube.

3. A connector comprising:

a housing provided with a fluid passage in its interior and a connection port for engagement with a tube; and a valve of an elastic material accommodated in said housing; wherein said valve has a cylindrical base which is tapered such that a wall thickness gradually increases toward a distal end; a valve portion on one axial end of said base which becomes in contact with said tube to be pushed inward by said tube; and a slit formed in said valve portion which opens when said valve portion is pushed inward, wherein the slit has a size such that said tube cannot penetrate through the slit upon opening of said slit; and said valve undergoes elastic deformation when said tube is engaged with said connection port of the housing by pushing said tube against said valve portion of the valve, and said slit opens as a result of said elastic deformation such that said base becomes compressed in the axial direction to become dilated, such that a base of which the wall thickness gradually increases toward the distal end causes a larger deformation on a proximal side than a distal side because of lower flexural strength on the proximal side.

4. A connector comprising:

a housing provided with a fluid passage in its interior and a connection port for engagement with a tube; and a valve of an elastic material accommodated in said housing; wherein said valve has a cylindrical base which is tapered such that a wall thickness gradually increases toward a distal end; a valve portion on one axial end of said base which becomes in contact with said tube to be pushed inward by said tube; and a slit formed in said valve portion which opens when said valve portion is pushed inward, wherein the slit has a size such that said tube cannot penetrate through the slit upon opening of said slit; and said valve undergoes elastic deformation when said tube is engaged with said connection port of the housing by pushing said tube against said valve portion of the valve, and said slit opens as a result of said elastic deformation, and a base of which the wall thickness gradually increases toward the distal end causes a larger deformation on a proximal side than a distal side because of lower flexural strength on the proximal side, such that said valve portion becomes in close contact with said tube and the area of contact enters the interior of said base.

5. A connector comprising:

a housing provided with a fluid passage in its interior and a connection port for engagement with a tube; and a valve of an elastic material accommodated in said housing; wherein said valve has a cylindrical base which is tapered such that a wall thickness gradually increases toward a distal end; a valve portion on one axial end of said base which becomes in contact with said tube to be pushed inward by said tube; and a slit formed in said valve portion which opens when said valve portion is pushed inward, wherein the slit has a size such that said tube cannot penetrate through the slit upon opening of said slit; and said valve undergoes elastic deformation when said tube is engaged with said connection port of the housing by pushing said tube against said valve portion of the valve, and said slit opens as a result of said elastic deformation with the base being dilated; and a space is defined between said base and said housing to allow said dilatation of the base and a base of which the wall thickness gradually increases toward the distal end causes a larger deformation on a proximal side than a distal side because of lower flexural strength on the proximal side.

6. A connector comprising:

a housing provided with a fluid passage in its interior and a connection port for engagement with a tube; and a valve of an elastic material accommodated in said housing; wherein said valve has a cylindrical base end; a valve portion on one axial end of said base which becomes in contact with said tube to be pushed inward by said tube; a slit formed in said valve portion which opens when said valve portion is pushed inward; and a fixture portion on the other axial end of said base, said fixture portion securing said valve against said housing; and said housing has a relief space defined in its interior to thereby allow moving of fixture portion of said base into said relief space;

said valve undergoes elastic deformation when said tube is engaged with said connection port of the housing by pushing said tube against said valve portion of the valve, and said slit opens as a result of said elastic deformation with the fixture portion of said base being pushed into said relief space.

7. A connector according to claim 6 wherein said base becomes compressed in the axial direction to become dilated when said tube is pushed against said valve portion of the valve.

8. A connector according to claim 6 wherein a space is defined between said base and said housing to allow said dilatation of said base.

9. A connector according to claim 1 wherein said valve restores its original shape when said tube is disengaged from said connection port.

10. A connector according to claim 1 wherein said valve portion has a thick area in the central region, and said slit is formed in said thick area.

11. A connector according to claim 1 wherein at least a part of said base is tapered such that outer diameter or inner diameter increases with increase in the distance from said valve portion.

12. A connector according to claim 1 wherein said valve portion has a projection and/or a recess on the surface that becomes in contact with said connection port of said tube.

13. A connector according to claim 12 wherein said valve portion has a first projection on the surface that becomes in contact with said connection port of the tube.

14. A connector according to claim 13 wherein said first projection has a shape resembling a dome.

15. A connector according to claim 1 wherein said valve portion has a projection on the surface that does not become in contact with said connection port of the tube.

16. A connector according to claim 15 wherein said projection constitutes a part of a sphere.

17. A connector comprising:

a housing provided with a fluid passage in its interior and a connection port for engagement with a tube; and a valve of an elastic material accommodated in said housing; wherein said valve has a cylindrical base which is tapered such that a wall thickness gradually increases toward a distal end; a valve portion on one axial end of said base which becomes in contact with said tube to be pushed inward by said tube; a slit formed in said valve portion which opens when said valve portion is pushed inward; and a fixture portion on the other axial end of said base, said fixture portion securing said valve against said housing, wherein the slit has a size such that said tube cannot penetrate through the slit upon opening of said slit; and said housing has a relief space defined in its interior to thereby allow moving of the fixture portion of said base into said relief space;

said valve undergoes elastic deformation when said tube is engaged with said connection port of the housing by pushing said tube against said valve portion of the valve, and said slit opens as a result of said elastic deformation and a base of which the wall thickness gradually increases toward the distal end causes a larger deformation on a proximal side than a distal side because of lower flexural strength on the proximal side, such that the fixture portion of said base being pushed into said relief space.

* * * * *